US008512594B2

(12) United States Patent
Walker et al.

(10) Patent No.: US 8,512,594 B2
(45) Date of Patent: Aug. 20, 2013

(54) CURING AGENT OF N,N'-DIMETHYL-META-XYLYLENEDIAMINE AND MULTIFUNCTIONAL AMIN(S)

(75) Inventors: Frederick Herbert Walker, Allentown, PA (US); Robert Marjo Theodoor Rasing, Didam (NL); Gamini Ananda Vedage, Bethlehem, PA (US); Michael Ian Cook, De Meern (NL); Peter Andrew Lucas, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 12/197,585

(22) Filed: Aug. 25, 2008

(65) Prior Publication Data

US 2010/0048827 A1 Feb. 25, 2010

(51) Int. Cl.
*C08G 59/56* (2006.01)
*C08G 59/60* (2006.01)
*C08K 5/05* (2006.01)
*C08L 63/00* (2006.01)
*C08L 63/02* (2006.01)
*C09D 163/00* (2006.01)
*C09D 163/02* (2006.01)
*C09K 3/00* (2006.01)

(52) U.S. Cl.
USPC ............. 252/182.13; 252/182.23; 523/400; 523/454; 523/455; 523/456; 525/407; 525/423; 525/504; 525/523; 528/122; 528/123; 528/124

(58) Field of Classification Search
None
See application file for complete search history.

(56) References Cited

U.S. PATENT DOCUMENTS

| 4,142,034 | A | * | 2/1979 | Schroll | ......................... 528/120 |
| 5,387,368 | A | | 2/1995 | Nishimura et al. | |
| 5,503,936 | A | | 4/1996 | Blyakhman | |
| 5,618,905 | A | | 4/1997 | Marsella et al. | |
| 2004/0220194 | A1 | | 11/2004 | Neustadt et al. | |
| 2007/0027345 | A1 | | 2/2007 | Hugo et al. | |
| 2008/0194776 | A1 | | 8/2008 | Walker et al. | |
| 2008/0275191 | A1 | | 11/2008 | Vedage et al. | |
| 2010/0048954 | A1 | * | 2/2010 | Vedage et al. | ................. 564/372 |

FOREIGN PATENT DOCUMENTS

| DE | 122258 | | 9/1976 |
| DE | 130580 | | 4/1978 |
| DE | 135623 | A | 5/1979 |
| DE | 3803508 | C2 | 4/1994 |
| DE | 103 41 612 | A1 | 4/2005 |
| EP | 1 279 661 | A | 1/2003 |
| JP | 62-283179 | | 12/1987 |
| JP | 02103221 | A | 4/1990 |
| JP | 05-140555 | | 6/1993 |
| JP | 06-306360 | | 11/1994 |
| JP | 2007-009230 | | 1/1997 |
| JP | 2008-291240 | | 12/2008 |
| JP | 2010-065031 | | 3/2010 |
| WO | 2005/005395 | A | 1/2005 |

OTHER PUBLICATIONS

Safety Emporuim, definition of amine, 2000, four pages.*
John G. Williams, The Beta Relaxation in Epoxy Resin-Based Networks, Journal of Applied Polymer Science, vol. 23, 3433-3444, 1979.
John A. Marsella, et al. Acceleration of Amine/Epoxy Reactions with N-Methyl Secondary Amines, Journal of Polymer Science, Part A, Polymer Chemistry, vol. 38,921-930 (2000).
Taizo Hatta, et al. Synthesis of Water-soluble diaza-1,2,5-thiadiazolocyclophanes, Heterocycles, vol. 46, 651-658, 1997.

* cited by examiner

*Primary Examiner* — Robert Sellers
(74) *Attorney, Agent, or Firm* — Michael K. Boyer

(57) ABSTRACT

The present invention discloses both amine compositions and amine-epoxy compositions containing N,N'-dimethyl-meta-xylylenediamine. A novel process for producing amines such as N,N'-dimethyl-meta-xylylenediamine, and structurally similar amines, is also disclosed.

18 Claims, No Drawings

CURING AGENT OF N,N'-DIMETHYL-META-XYLYLENEDIAMINE AND MULTIFUNCTIONAL AMIN(S)

BACKGROUND OF THE INVENTION

The present invention is directed generally to N,N'-dimethyl-meta-xylylenediamine (DM-MXDA) and to methods for producing DM-MXDA and related amines. The present invention also relates to amine compositions and amine-epoxy compositions containing DM-MXDA, methods of making amine-epoxy compositions, and articles, such as coatings, composites, and civil engineering products, produced from these amine-epoxy compositions.

Epoxy resins which are cured, hardened, or crosslinked with multifunctional amines, i.e., amine compounds having three or more active amine hydrogens, are well known in the industry. These materials are widely used in applications such as coatings, composites, and civil engineering applications, for example, formulations for flooring. In coating applications, some amine-cured epoxy formulations can be cured at room temperature to yield films with high mechanical strength, good water, chemical, and corrosion resistance, and excellent adhesion properties, particularly to metallic substrates. Thus, they are often employed as primers and topcoats for large structures such as ships, bridges, and industrial plants and equipment. Some amine-epoxy formulations provide excellent adhesion to concrete and other cementitious materials and, therefore, are often employed in sealers, primers, coatings, mortars, and grouts for concrete and other cementitious materials.

Before regulations placing limits on the volatile organic compound (VOC) content of amine-epoxy coatings, formulations were often based on solid epoxy resins. These resins are solid at room temperature. Coatings using solid epoxy resins usually dried very quickly, since only solvent evaporation, not chemical cure, was required for the coating to reach a dry-to-touch state.

Due to the VOC regulations, epoxy resins that are liquids at room temperature have replaced solid epoxy resins in many applications. This transition has resulted in several problems, for example, in coating applications. Amine-epoxy compositions based upon liquid epoxy resins tend to cure much more slowly than a comparable solid epoxy resin formulation, and this problem becomes more severe at lower temperatures. Shipyards, for example, often reside in locations with cold winters, and paint must be applied when temperatures are about 5° C. or colder. Many amine-epoxy coating formulations cure very slowly at these temperatures, often requiring at least 24 hours, and in some cases much more than 24 hours, to reach the "walk-on" dry state required so that painters can apply a second or third coat, if required. In the laboratory, the "walk-on" dry state is often estimated by the thumb-twist test method. Slow drying times can dramatically impact a shipyard's productivity. Thus, fast cure speed at below room temperature is a desirable property in many applications.

It is also beneficial to limit the volatility of the amine component in the amine-epoxy formulation. In addition to meeting VOC regulations, reducing volatility can reduce worker exposure and safety concerns.

Amine-epoxy coating formulations based on a liquid epoxy resin, as opposed to a solid epoxy resin, can also be less flexible than required for certain applications. For example, in ships employing modern double hull construction, the steel used in the two hulls that form the ballast tank is a thinner gauge than used in single hull ships. As a result of the thinner gauge, the steel flexes more which can lead to a stress crack failure of the coating, especially around welded joints. This in turn can lead to corrosion, which can be expensive to repair and can affect the ship's integrity. Further, in the rail car industry, there are also problems due to lack of coating flexibility at the weld seams. Additionally, coatings in many other applications require greater flexibility, for example, to achieve a desired impact resistance for a given application, or to post-form a metal after painting. In the end-use application, the amount of stress or deformation that the material undergoes, as well as the rate of deformation, are important factors for determining the flexibility required, and thus the suitability of a particular amine-epoxy composition or formulation. In civil engineering applications, for example, those involving concrete and other cementitious materials, amine-epoxy materials capable of withstanding greater expansion and contraction stresses, and capable of meeting crack bridging requirements, are also of interest.

Many epoxy coatings are over-coated with a second or third coating. The additional coatings are not limited to epoxy-based systems and can include other chemical coating systems (e.g., polyurethanes) in order to provide particular end-use properties, such as corrosion resistance, weatherability, etc. Intercoat adhesion in formulations based on liquid epoxy resins typically is less than comparable solid epoxy resin formulations, often leading to intercoat adhesion failures. Even when adequate intercoat adhesion for a liquid epoxy system is obtained, re-coating often must occur within a limited time frame if intercoat adhesion failures are to be avoided. This time is often referred to as the re-coat window.

Many amine-epoxy coatings suffer from problems referred to in the industry as blush, carbamation, and exudate. These problems, in part, are due to the incompatibility of the amine curing agent and the epoxy resin, which causes phase separation and results in amine migration to the coating surface. In primary amines, the migratory amine can react with $CO_2$ present in the air, resulting in carbamation. Whether in the form of carbamation or the greasy surface layer referred to as exudate or blush, these surface defects detract from the appearance of the coating, and can lead to intercoat adhesion failures if the film is re-coated. These problems are generally worse for coatings applied and cured at colder temperatures, where amine-epoxy compatibility is reduced.

Often, epoxy coatings used in some of the aforementioned applications, such as coatings on metal, concrete, and cementitious substrates, require good chemical, water, and corrosion resistance. These barrier and weatherability properties of the coating can be important attributes to protect the substrate from environmental impact.

There are several broad classes of multifunctional amine curing agents that are employed in the amine-epoxy coating industry, including polyamides, Mannich bases (including phenalkamines), and amine adducts. None of these known products addresses the needs or solves the problems noted above. Accordingly, it is to this end that the present invention is directed.

BRIEF SUMMARY OF THE INVENTION

The present invention discloses both amine compositions and amine-epoxy compositions containing N,N'-dimethyl-meta-xylylenediamine (DM-MXDA). Amine compositions can be used, for example, to cure, harden, or crosslink an epoxy resin. In accordance with one aspect of the present invention, the amine composition comprises:

(i) DM-MXDA; and (ii) at least one multifunctional amine selected from an arene amine; an aromatic amine; a Mannich base derivative of an aliphatic amine, a cycloaliphatic amine, an arene amine, or an aromatic amine; a polyamide derivative of an aliphatic amine, a cycloaliphatic amine, an arene amine, or an aromatic amine; an amidoamine derivative of an aliphatic amine, a cycloaliphatic amine, an arene amine, or an aromatic amine; and an amine adduct derivative of an aliphatic amine, a cycloaliphatic amine, an arene amine, or an aromatic amine; or any combination thereof.

In accordance with another aspect of this invention, the amine composition comprises:

(i) N,N'-dimethyl-meta-xylylenediamine (DM-MXDA); and (ii) at least one multifunctional amine having 3 or more active amine hydrogens;

wherein a weight ratio of DM-MXDA to the at least one multifunctional amine is in a range from about 65:35 to about 1:99.

In accordance with still another aspect of this invention, the amine composition comprises:

(i) N,N'-dimethyl-meta-xylylenediamine (DM-MXDA); and (ii) at least one multifunctional amine selected from a phenalkamine; meta-xylylene diamine (MXDA); 1,3-bis(aminomethyl)cyclohexane (1,3-BAC); and a mixture of methylene bridged poly(cyclohexyl-aromatic)amines (MPCA); or any combination thereof.

In accordance with yet another aspect of this invention, an amine composition comprises:

(i) N,N'-dimethyl-meta-xylylenediamine (DM-MXDA);

(ii) at least one multifunctional amine having 3 or more active amine hydrogens; and (iii) optionally, at least one plasticizer or solvent.

In an embodiment of this aspect of the invention an amine composition, which is directed to end-uses such as coatings, civil engineering applications, and the like, comprises at least one plasticizer or solvent.

The present invention also discloses amine-epoxy compositions. These compositions can comprise (a) any of the four aforementioned amine compositions, provided immediately above; and (b) an epoxy component comprising at least one multifunctional epoxy resin. Compositions obtained by curing the amine-epoxy compositions of the present invention, as well as articles of manufacture comprising these compositions, are also contemplated herein. Such articles can include, for example, a coating, a construction product, a flooring product, a composite product, and the like.

Novel processes for producing amines such as DM-MXDA, and structurally similar amines, are also described in the present invention. Amine compounds having the formula:

$$(R^C)_X \underset{CH_2NHR^B}{\overset{CH_2NHR^A}{\diagup\!\!\!\!\diagdown}} \quad (I)$$

can be produced by a process comprising:

(a) contacting a compound having the formula:

$$(R^C)_X \text{—} \bigcirc \text{—} (CN)_2 \quad (II)$$

with methylamine or ethylamine in the presence of hydrogen and a catalyst at a hydrogen pressure of about 100 to about 500 psi to form at least one intermediate product; and (b) contacting the at least one intermediate product with hydrogen in the presence of a hydrogenation catalyst at a hydrogen pressure of about 400 to about 1500 psi to form the amines having formula (I);

wherein:

$R^A$ is methyl or ethyl;

$R^B$ is methyl, ethyl, or hydrogen;

$R^C$ in each occurrence is selected independently from a linear or branched $C_1$-$C_{18}$ alkyl, a linear or branched $C_1$-$C_{18}$ alkenyl, a linear or branched $C_1$-$C_{18}$ alkoxy, and a linear or branched $C_1$-$C_{18}$ alkoxyalkyl; and x is 0, 1, 2, 3, or 4.

A process is also disclosed for producing a mixture of amines comprising DM-MXDA. This process comprises:

(a) contacting 1,3-dicyanobenzene with mono-methylamine in the presence of hydrogen and a catalyst at a hydrogen pressure of about 100 to about 500 psi to form at least one intermediate product;

(b) contacting the at least one intermediate product with hydrogen in the presence of a hydrogenation catalyst at a hydrogen pressure of about 400 to about 1500 psi to form the mixture of amines comprising DM-MXDA.

This process can produce a mixture of amines in which the yield of DM-MXDA in the mixture of amines is at least about 60% by weight. For example, the yield of DM-MXDA in the mixture of amines can be 70% by weight, or more.

DEFINITIONS

The following definitions and abbreviations are provided in order to aid those skilled in the art in understanding the detailed description of the present invention. To the extent that any definition or usage provided by any document incorporated herein by reference conflicts with the definition or usage provided herein, the definition or usage provided herein controls.

1,3-BAC—1,3-bis(aminomethyl)cyclohexane, commercially available from Mitsubishi Chemical Corporation, AHEW=36.

A1618—Ancamine® 1618, commercially available from Air Products and Chemicals, cycloaliphatic amine adduct, Inc., AHEW=115.

A2050—Ancamide® 2050, commercially available from Air Products and Chemicals, polyamide adduct, AHEW=150.

A2603—Ancamine® 2603, commercially available from Air Products and Chemicals, aliphatic amine adduct, AHEW=175.

AHEW—Amine hydrogen equivalent weight.

BA—Benzyl alcohol, commercially available from Fisher Scientific UK Ltd.

CX-105—Sunmide® CX-105, commercially available from Air Products and Chemicals, Inc., phenalkamine, AHEW=142.

DCB—1,3-dicyanobenzene, also referred to as isophtha-lonitrile, commercially available from Aldrich Chemical Co.

DGEBA—Diglycidyl ether of bisphenol-A.

DM-MXDA—N,N'-dimethyl-meta-xylylenediamine, also referred to as 1,3-bis[(N-methylamino)methyl]benzene or 1,3-bis(azapropyl)benzene, calculated AHEW=82.

DM-HMDA—N,N'-dimethyl-1,6-hexamethylenedi-amine, commercially available from Aldrich Chemical Co., AHEW=72.

EEW—Epoxy equivalent weight.

IPDA—Isophorone diamine, commercially available from Degussa AG, AHEW=43.

K54—Ancamine® K54, commercially available from Air Products and Chemicals, Inc., tris-(dimethylaminom-ethyl)phenol.

MMA—Methylamine or mono-methylamine, commercially available from Aldrich Chemical Co.

MM-MXDA—N-monomethyl-meta-xylylenediamine, AHEW=50.

$M_n$—Number-average molecular weight.

MPCA—Also abbreviated as MBPCAA. MPCA is a mixture of methylene bridged poly(cyclohexyl-aromatic) amines that fits within the class of multifunctional amines. Ancamine® 2168, commercially available from Air Products and Chemicals, Inc., is a MPCA with an AHEW of 57 and is the grade utilized in the examples.

MXDA—Meta-xylylene diamine, also referred to as 1,3-bis[(amino)methyl] benzene, commercially available from Mitsubishi Chemical Corporation, AHEW=34.

NC541LV—Cardolite® NC541 LV, commercially available from Cardolite Corporation, low viscosity phe-nalkamine, AHEW=125.

PHR—Parts per hundred weight resin.

THF—Tetrahydrofuran.

Applicants disclose several types of ranges in the present invention. These include, but are not limited to, a range of temperatures, a range of pressures, a range of reaction times, a range of number of atoms, a range of integers, a range of weight ratios, and a range of stoichiometric ratios. When Applicants disclose or claim a range of any type, Applicants' intent is to disclose or claim individually each possible number that such a range could reasonably encompass, as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that "$R^C$" can be a $C_1$ to $C_{18}$ linear or branched alkyl, alkenyl, alkoxy, or alkoxyalkyl, or in alternative language having from 1 to 18 carbon atoms, as used herein, refers to a "$R^C$" group that can be selected independently from a linear or branched alkyl, alkenyl, alkoxy, or alkoxyalkyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_{10}$ linear or branched alkyl, alkenyl, alkoxy, or alkoxyalkyl group), and also including any combination of ranges between these two numbers (for example, a $C_2$ to $C_6$ and $C_9$ to $C_{15}$ linear or branched alkyl, alkenyl, alkoxy, or alkoxyalkyl group).

Similarly, another representative example follows for the weight ratio of DM-MXDA to the at least one multifunctional amine in an amine composition. By a disclosure that the weight ratio of DM-MXDA to the at least one multifunctional amine is in a range from about 95:5 to about 5:95, Applicants intend to recite that the weight ratio can be selected from about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, or about 5:95. Additionally, the weight ratio can be within any range from about 95:5 to about 5:95 (for example, the weight ratio is in a range from about 65:35 to about 20:80), and this includes any combination of ranges between about 95:5 to about 5:95 (for example, the weight ratio is in a range from about 90:10 to about 70:30, or from about 50:50 to about 25:75). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions or formulations described herein. Combining additional materials or components can be done by any method known to one of skill in the art. Further, the term "contact product" includes mixtures, blends, solutions, slurries, reaction products, and the like, or combinations thereof. Although "contact product" can encompass reaction products of two or more components, it is not required for the respective components to react with one another.

While compositions and methods are described in terms of "comprising" various components or steps, the compositions and methods can also "consist essentially of" or "consist of" the various components or steps.

DETAILED DESCRIPTION OF THE INVENTION

Amine Compositions

The present invention discloses amine compositions comprising N,N'-dimethyl-meta-xylylenediamine (DM-MXDA). Such compositions can be used, for example, to cure, harden, or crosslink an epoxy resin. An amine composition in accordance with one aspect of this invention comprises:

(i) DM-MXDA; and (ii) at least one multifunctional amine selected from an arene amine; an aromatic amine; a Mannich base derivative of an aliphatic amine, a cycloaliphatic amine, an arene amine, or an aromatic amine; a polyamide derivative of an aliphatic amine, a cycloaliphatic amine, an arene amine, or an aromatic amine; an amidoamine derivative of an aliphatic amine, a cycloaliphatic amine, an arene amine, or an aromatic amine; and an amine adduct derivative of an aliphatic amine, a cycloaliphatic amine, an arene amine, or an aromatic amine; or any combination thereof.

In another aspect, the weight ratio of DM-MXDA to the at least one multifunctional amine in this amine composition ranges from about 95:5 to about 5:95. In yet another aspect, the weight ratio of DM-MXDA to the at least one multifunctional amine ranges from about 80:20 to about 20:80, or from about 70:30 to about 30:70. These ratios are based only on the amine components in the compositions, and do not include other components that could be present in an amine composition, such as plasticizers or solvents, pigments, fillers, and the like. However, if more than one multifunctional amine were employed, then the total amount of multifunctional amine would be used in determining the ratio of DM-MXDA to multifunctional amine. In amine-epoxy coating applications, incorporating higher levels of DM-MXDA relative to the amount of multifunctional amine(s) generally results in coatings that cure faster and/or can be cured at lower temperatures, and which have greater flexibility and a longer re-coat window. Incorporating higher levels of multifunctional amine(s) relative to the amount of DM-MXDA generally improves the chemical resistance of the product, and can result in coatings with higher ultimate hardness.

Additionally, N-monomethyl-meta-xylylenediamine (MM-MXDA) can be an at least one multifunctional amine in these amine compositions. That is, an amine composition can comprise DM-MXDA and MM-MXDA, or alternatively, can comprise DM-MXDA, MM-MXDA, and at least one other multifunctional amine. In this aspect, the at least one other multifunctional amine can be selected from an arene amine; an aromatic amine; a Mannich base derivative of an aliphatic amine, a cycloaliphatic amine, an arene amine, or an aromatic amine; a polyamide derivative of an aliphatic amine, a cycloaliphatic amine, an arene amine, or an aromatic amine; an amidoamine derivative of an aliphatic amine, a cycloaliphatic amine, an arene amine, or an aromatic amine; and an amine adduct derivative of an aliphatic amine, a cycloaliphatic amine, an arene amine, or an aromatic amine; or any combination thereof.

An amine composition in accordance with another aspect of this invention comprises:
(i) N,N'-dimethyl-meta-xylylenediamine (DM-MXDA); and
(ii) at least one multifunctional amine having 3 or more active amine hydrogens;
wherein a weight ratio of DM-MXDA to the at least one multifunctional amine is in a range from about 65:35 to about 1:99.

In a further aspect, the weight ratio of DM-MXDA to the at least one multifunctional amine in this amine composition can fall within a range from about 60:40 to about 5:95. Still further, the weight ratio of DM-MXDA to the at least one multifunctional amine can range from about 55:45 to about 10:90, or from about 50:50 to about 20:80, in other aspects of this invention. For instance, an amine composition of this invention can comprise DM-MXDA and MM-MXDA, or DM-MXDA, MM-MXDA, and at least one other multifunctional amine, wherein the weight ratio of DM-MXDA to the at least one multifunctional amine is in a range from about 65:35 to about 1:99. In compositions where more than one multifunctional amine is employed (e.g., MM-MXDA and MPCA), the total amount of multifunctional amine is used in determining the ratio of DM-MXDA to multifunctional amine.

An amine composition in accordance with still another aspect of this invention comprises:
(i) N,N'-dimethyl-meta-xylylenediamine (DM-MXDA); and
(ii) at least one multifunctional amine selected from a phenalkamine; meta-xylylene diamine (MXDA); 1,3-bis (aminomethyl)cyclohexane (1,3-BAC); and a mixture of methylene bridged poly(cyclohexyl-aromatic)amines (MPCA); or any combination thereof.

The weight ratio of DM-MXDA to the at least one multifunctional amine (a phenalkamine; MXDA; 1,3-BAC; or MPCA) in this amine composition can range from about 95:5 to about 5:95 in some aspects of this invention. For example, the weight ratio of DM-MXDA to the at least one multifunctional can range from about 90:10 to about 10:90, from about 80:20 to about 20:80, or from about 70:30 to about 30:70. N-monomethyl-meta-xylylenediamine (MM-MXDA) also can be present as an additional multifunctional amine in these amine compositions. An amine composition within the scope of this invention, therefore, can comprise DM-MXDA, MM-MXDA, and a phenalkamine. Alternatively, amine compositions can comprise DM-MXDA, MM-MXDA, and MXDA; or DM-MXDA, MM-MXDA, and 1,3-BAC; or DM-MXDA, MM-MXDA, and MPCA.

Yet, in accordance with another aspect of this invention, an amine comprises:
(i) N,N'-dimethyl-meta-xylylenediamine (DM-MXDA);
(ii) at least one multifunctional amine having 3 or more active amine hydrogens; and
(iii) optionally, at least one plasticizer or solvent.

In an embodiment of this aspect of the invention an amine composition, which is directed to end-uses such as coatings, civil engineering applications, and the like, comprises at least one plasticizer or solvent.

Generally, the weight ratio of DM-MXDA to the at least one multifunctional amine in this amine composition ranges from about 95:5 to about 5:95, for example, a range from about 90:10 to about 10:90. Weight ratios of DM-MXDA to the at least one multifunctional amine ranging from about 80:20 to about 20:80, or from about 70:30 to about 30:70, can be employed in other aspects of this invention. The amine compositions for coating and civil engineering applications can utilize N-monomethyl-meta-xylylenediamine (MM-MXDA) as an at least one multifunctional amine. One such composition, for example, comprises DM-MXDA, MM-MXDA, at least one other multifunctional amine having 3 or more active amine hydrogens, and at least one plasticizer or solvent.

Amine-Epoxy Compositions

The present invention discloses amine-epoxy compositions comprising N,N'-dimethyl-meta-xylylenediamine (DM-MXDA), and methods of making these compositions. These amine-epoxy compositions can comprise any of the aforementioned amine compositions provided in the section above and an epoxy component comprising at least one multifunctional epoxy resin. For example, an amine-epoxy composition can comprise:
(a) an amine composition comprising:
(i) DM-MXDA; and
(ii) at least one multifunctional amine selected from an arene amine; an aromatic amine; a Mannich base derivative of an aliphatic amine, a cycloaliphatic amine, an arene amine, or an aromatic amine; a polyamide derivative of an aliphatic amine, a cycloaliphatic amine, an arene amine, or an aromatic amine; an amidoamine derivative of an aliphatic amine, a cycloaliphatic amine, an arene amine, or an aromatic amine; and an amine adduct derivative of an aliphatic amine, a cycloaliphatic amine, an arene amine, or an aromatic amine; or any combination thereof; and
(b) an epoxy component comprising at least one multifunctional epoxy resin.

An amine-epoxy composition in another aspect of this invention comprises:
(a) an amine composition comprising:
(i) DM-MXDA; and
(ii) at least one multifunctional amine having 3 or more active amine hydrogens; wherein a weight ratio of DM-MXDA to the at least one multifunctional amine is in a range from about 65:35 to about 1:99; and
(b) an epoxy component comprising at least one multifunctional epoxy resin.

An amine-epoxy composition in yet another aspect of this invention comprises:
(a) an amine composition comprising:
(i) DM-MXDA; and
(ii) at least one multifunctional amine selected from a phenalkamine; meta-xylylene diamine (MXDA); 1,3-bis(aminomethyl)cyclohexane (1,3-BAC); and a mixture of methylene bridged poly(cyclohexyl-aromatic) amines (MPCA); or any combination thereof; and
(b) an epoxy component comprising at least one multifunctional epoxy resin.

In a further aspect, the present invention contemplates methods for curing these amine-epoxy compositions. This invention is not limited to any particular temperature and humidity conditions to cure these amine-epoxy compositions, nor to any specified cure time. However, the amine-epoxy compositions disclosed herein can be cured at room temperature and below, that is, at a temperature of less than or equal to about 23-25° C. In another aspect, the amine-epoxy compositions can be cured at a temperature of less than or equal to about 5° C. The amine-epoxy compositions of the present invention offer improved cure rates at temperatures at or below room temperature, including temperatures less than or equal to about 5° C., as compared to conventional amine-epoxy compositions.

Compositions obtained by curing the amine-epoxy compositions of the present invention, as well as articles of manufacture comprising these compositions, are also contemplated by the present invention. Such articles can include, but are not limited to, a coating, a construction product, a flooring product, a composite product, and the like. For example, the article can be a coating which is applied to a metal or cementitious substrate. Generally, coatings produced from amine-epoxy compositions of the present invention cure rapidly at temperatures of about 5° C. and lower, yielding coatings with good appearance, flexibility, and barrier properties. Additional components or additives can be used together with the compositions of the present invention to produce various articles of manufacture.

The present invention also provides methods of making an amine-epoxy resin composition. One such method comprises:
(a) forming an amine composition comprising DM-MXDA and at least one multifunctional amine; and
(b) contacting the amine composition with an epoxy component comprising at least one multifunctional epoxy resin at a stoichiometric ratio of epoxy groups in the epoxy component to amine hydrogens in the amine composition ranging from about 5:1 to about 1:1.5.

In accordance with the amine-epoxy compositions and methods of making an amine-epoxy composition disclosed herein, the stoichiometric ratio of epoxy groups in the epoxy component to amine hydrogens in the amine composition generally ranges from about 5:1 to about 1:1.5. Yet, in some aspects, the stoichiometric ratio of epoxy groups in the epoxy component to amine hydrogens in the amine composition ranges from about 2:1 to about 1:1.2. For example, the stoichiometric ratio can be in a range from about 1.8:1 to about 1:1.1, or from about 1.6:1 to about 1:1. These stoichiometric ratios are based on the total quantities of the respective amine and epoxy components. For example, if the amine composition contains 65 parts by weight of DM-MXDA and 35 parts by weight of a multifunctional amine, the total amount of amine hydrogens from both the DM-MXDA and the multifunctional amine are used to determine the stoichiometric ratio.

Additionally, it can be beneficial in the compositions of the present invention for all of the possible components to be liquids at room temperature. That is, the DM-MXDA, the at least one multifunctional amine compound, and the at least one multifunctional epoxy resin compound can all be liquids at room temperature. In this disclosure, room temperature, or ambient temperature, is approximately 23-25° C.

According to another aspect of the invention, an amine-epoxy composition directed to end-uses such as coatings, civil engineering applications, and the like, is provided. Such an amine-epoxy composition comprises:
(a) an amine composition comprising:
(i) DM-MXDA;
(ii) at least one multifunctional amine having 3 or more active amine hydrogens; and
(iii) at least one plasticizer or solvent; and
(b) an epoxy component comprising at least one multifunctional epoxy resin.

Further, the present invention contemplates methods for curing this amine-epoxy composition. As with the amine-epoxy compositions disclosed above, the curing conditions for this amine-epoxy composition are not limited to any particular temperature, humidity, or cure time. This amine-epoxy composition can be cured at a temperature of less than or equal to about 23-25° C., or less than or equal to about 5° C., for example. Coatings and civil engineering products obtained by curing amine-epoxy compositions are also within the scope of the present invention. Often, coatings of this invention are applied to metal or cementitious substrates.

Methods of making a cured amine-epoxy coating are disclosed herein. One such process for producing a cured amine-epoxy coating in accordance with the present invention comprises:
(a) contacting an epoxy component comprising at least one multifunctional epoxy resin with an amine composition for coating applications to form an amine-epoxy coating composition;
(b) forming an uncured coating from the amine-epoxy coating composition; and
(c) curing the uncured coating to form the cured amine-epoxy coating; wherein the amine composition for coating applications comprises:
(i) DM-MXDA; and
(ii) at least one multifunctional amine having 3 or more active amine hydrogens.

In this method, the amine composition for coating applications can further comprise at least one plasticizer or solvent. Illustrative examples of suitable plasticizers or solvents include, but are not limited to, benzyl alcohol, n-butanol, xylene, methyl ethyl ketone, nonyl phenol, dodecyl phenol, cardanol, an ester of phthalic acid, and the like, or combinations thereof.

For the amine-epoxy coating compositions and methods of making a cured amine-epoxy coating provided above, the stoichiometric ratio of epoxy groups in the epoxy component to amine hydrogens in the amine coating composition generally ranges from about 5:1 to about 1:1.5. Often, the stoichiometric ratio of epoxy groups in the epoxy component to amine hydrogens in the amine coating composition is within a narrower range from about 2:1 to about 1:1.2.

Synthesizing DM-MXDA and Related Amines

N,N'-dimethyl-meta-xylylenediamine (DM-MXDA) and other amines that can be utilized in the amine compositions and amine-epoxy compositions disclosed herein can be prepared via any method known in the art. However, the present invention also provides an improved method for synthesizing amines such as DM-MXDA, and those that are structurally similar. Generally, the process involves two stages. The first stage is a reaction between a dicyanobenzene compound and either methylamine or ethylamine. The second stage is a hydrogenation reaction. The process can be used to produce amine compounds having the formula:

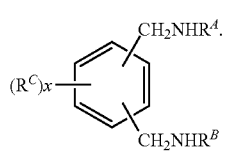
(I)

In one aspect of this invention, the process to produce amines having formula (I) comprises:

(a) contacting a compound having the formula:

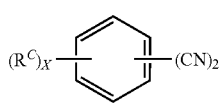
(II)

with methylamine or ethylamine in the presence of hydrogen and a catalyst at a hydrogen pressure of about 100 to about 500 psi to form at least one intermediate product; and (b) contacting the at least one intermediate product with hydrogen in the presence of a hydrogenation catalyst at a hydrogen pressure of about 400 to about 1500 psi to form the amines having formula (I);

wherein:

$R^A$ is methyl or ethyl;

$R^B$ is methyl, ethyl, or hydrogen;

$R^C$ in each occurrence is selected independently from a linear or branched $C_1$-$C_{18}$ alkyl, a linear or branched $C_1$-$C_{18}$ alkenyl, a linear or branched $C_1$-$C_{18}$ alkoxy, and a linear or branched $C_1$-$C_{18}$ alkoxyalkyl; and x is 0, 1, 2, 3, or 4.

Formulas (I) and (II) are not designed to show stereochemistry or isomeric positioning of the different moieties (e.g., these formulas are not intended to show cis or trans isomers), although such compounds are contemplated and encompassed by these formulas. In formula (I), $R^A$ is methyl or ethyl, while $R^B$ is methyl, ethyl, or hydrogen. The integer x in formulas (I) and (II) is 0, 1, 2, 3, or 4. For instance, when x is equal to zero, the compound of formula (II) can be 1,3-dicyanobenzene. All isomeric (ortho, meta and para) positions of the cyano groups in formula (II) can be employed and are within the scope of this invention. The integer x can be equal to zero in one aspect of this invention.

When x is not equal to zero, $R^C$ is selected independently from a linear or branched $C_1$-$C_{18}$ alkyl, alkenyl, alkoxy, or alkoxyalkyl. Unless otherwise specified, alkyl, alkenyl, alkoxy, or alkoxyalkyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, decyl, docedyl, and the like. Other alkyl groups such as, for example, a $C_{14}$ alkyl, a $C_{15}$ alkyl, a $C_{16}$ alkyl, a $C_{18}$ alkyl, and the like, can also be used in this invention. In formulas (I) and (II), $R^C$ can be an alkenyl group, examples of which include, but are not limited to, ethenyl, propenyl, butenyl, pentenyl, hexenyl, heptenyl, octenyl, nonenyl, decenyl, and the like, as well as $C_{14}$ alkenyl, $C_{15}$ alkenyl, $C_{16}$ alkenyl, or $C_{18}$ alkenyl groups. Alkoxy groups having up to 18 carbon atoms are within the scope of the present invention. Illustrative and non-limiting examples of suitable alkoxy groups include methoxy, ethoxy, propoxy, butoxy, and the like. An alkoxyalkyl group is also referred to as an ether group, examples of which include, but are not limited to, methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, and the like. As described herein, a linear or branched $C_1$-$C_{18}$ alkoxyalkyl is meant to have 1 to 18 carbon atoms, independently, on each side of the oxygen atom.

In one aspect of the present invention, each $R^C$ independently is a linear or branched $C_1$-$C_{18}$ alkyl or alkenyl. In another aspect, each $R^C$ independently is a methyl, ethyl, propyl, butyl, pentyl, hexyl, heptyl, octyl, nonyl, decyl, or docedyl group. Yet, in another aspect, each $R^C$ independently is an ethenyl, propenyl, butenyl, pentenyl, hexenyl, heptenyl, octenyl, nonenyl, or decenyl group. In a different aspect, each $R^C$ independently is a linear or branched $C_1$-$C_{18}$ alkoxy such as, for example, methoxy, ethoxy, propoxy, or butoxy. Alternatively, each $R^C$ independently can be a linear or branched $C_1$-$C_{18}$ alkoxyalkyl, examples of which are methoxymethyl, methoxyethyl, ethoxymethyl, ethoxyethyl, propoxymethyl, propoxyethyl, butoxymethyl, and butoxyethyl. In another aspect, each $R^C$ independently is a linear $C_1$-$C_4$ alkyl, alkenyl, alkoxy, or alkoxyalkyl. In these and other aspects, x is equal to 1, 2, 3, or 4. For instance, x can be equal to 1, and $R^C$ can be a linear $C_1$-$C_4$ alkyl, alkenyl, alkoxy, or alkoxyalkyl.

In the first stage of the process to produce amines having formula (I), provided above as step (a), a compound having the formula:

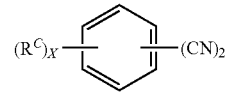
(II)

is contacted with methylamine or ethylamine in the presence of hydrogen and a catalyst. Generally, this reaction is conducted under a hydrogen atmosphere at a pressure in the range from about 100 to about 500 psi. For example, the reaction pressure can be controlled at a pressure in a range from about 200 to about 450 psi, or in a range from about 300 to about 400 psi. In one aspect, the hydrogen pressure is maintained in a range from about 300 to about 350 psi.

The reaction temperature for step (a) typically falls within a range from about 70 to about 160° C. Often, this reaction is conducted at a temperature in a range from about 80 to about 150° C., for example, in a range from about 100 to about 140° C., or from about 120 to about 140° C. Reaction time depends greatly on the reaction temperature, but is generally in the range from about 1 to about 20 hours. For instance, reaction times of 5 to 16 hours can be employed.

The catalyst used for the first stage of the process can comprise, for example, palladium, platinum, rhodium, Raney nickel, or any combination thereof, but the catalyst selection is not limited to only these metals. The metal catalyst can be supported on a variety of support materials including, but not limited to, carbon, silica, alumina, and the like, or mixtures thereof. Mixed oxide supports can also be used, such as silica-alumina.

According to another aspect of the present invention, the at least one intermediate reaction product of step (a) is vented prior to the second stage. For example, the reaction product can contain ammonia and/or unreacted methylamine or ethylamine which is vented or removed from the reactor. Generally, in this aspect, at least 50% by weight of the ammonia and/or unreacted methylamine or ethylamine is removed prior to the second stage. Further, at least 70% by weight, or at least 90% by weight, of the ammonia and/or unreacted methylamine or ethylamine can be removed prior to the second stage. Yet, in another aspect, substantially all of the ammonia and/or unreacted methylamine or ethylamine is removed prior to the second stage of the process.

In step (b), the second stage of the process, the at least one intermediate product from the first stage is contacted with hydrogen in the presence of a hydrogenation catalyst at a hydrogen pressure of about 400 to about 1500 psi to form the amines having formula (I). The hydrogenation reaction is conducted under a hydrogen atmosphere at pressures which are often higher than in the first stage. For example, hydrogenation reaction pressures in the range from about 600 to about 1200 psi, or from about 750 to about 1000 psi, are often utilized. In some aspects of this invention, a hydrogen pressure in the range from about 800 to about 950 psi can be employed.

The reaction temperature for the hydrogenation step is generally within a range from about 80 to about 160° C. Temperatures in the range from about 100 to about 140° C., from about 110 to about 130° C., or from about 120 to about 130° C., can be used in others aspects of this invention. As with the first stage, reaction time for the hydrogenation step depends greatly on the reaction temperature, but is generally in the range from about 45 to about 360 minutes. For instance, reaction times of 60 to 300 minutes can be employed.

The hydrogenation catalyst used for the second stage can comprise, for example, palladium, platinum, Raney nickel, Raney cobalt, or any combination thereof, but the hydrogenation catalyst is not limited to only these metals. As with the catalyst employed in the first stage reaction, the metal catalyst in the hydrogenation stage can be supported on a variety of support materials including, but not limited to, carbon, silica, alumina, and the like, or mixtures thereof. Mixed oxide supports can also be used, such as silica-alumina. Additionally, in one aspect of the present invention, the catalyst employed in the first stage of the process is the same as the hydrogenation catalyst employed in the hydrogenation stage. Alternatively, the catalyst of the first stage can be removed, for example, by filtration, prior to the second stage.

In accordance with the present invention, a process for producing a mixture of amines comprising N,N'-dimethyl-meta-xylylenediamine (DM-MXDA) is provided. This process comprises:

(a) contacting 1,3-dicyanobenzene with mono-methylamine in the presence of hydrogen and a catalyst at a hydrogen pressure of about 100 to about 500 psi to form at least one intermediate product;

(b) contacting the at least one intermediate product with hydrogen in the presence of a hydrogenation catalyst at a hydrogen pressure of about 400 to about 1500 psi to form the mixture of amines comprising DM-MXDA.

The same temperature, time, pressure, and catalyst selections for steps (a) and (b) discussed above relative to the process of producing amines having formula (I) also apply to this process for producing a mixture of amines comprising DM-MXDA. For example, step (a) can be conducted at a temperature of about 70 to about 160° C. and at a hydrogen pressure of about 200 to about 450 psi, while hydrogenation step (b) can conducted at a temperature of about 80 to about 160° C. and at a hydrogen pressure of about 750 to about 1000 psi. Additionally, in another aspect of this invention, the catalyst utilized in step (a) and the hydrogenation catalyst in step (b) can be the same.

This process for producing a mixture of amines comprising DM-MXDA is illustrated in the general reaction scheme presented below:

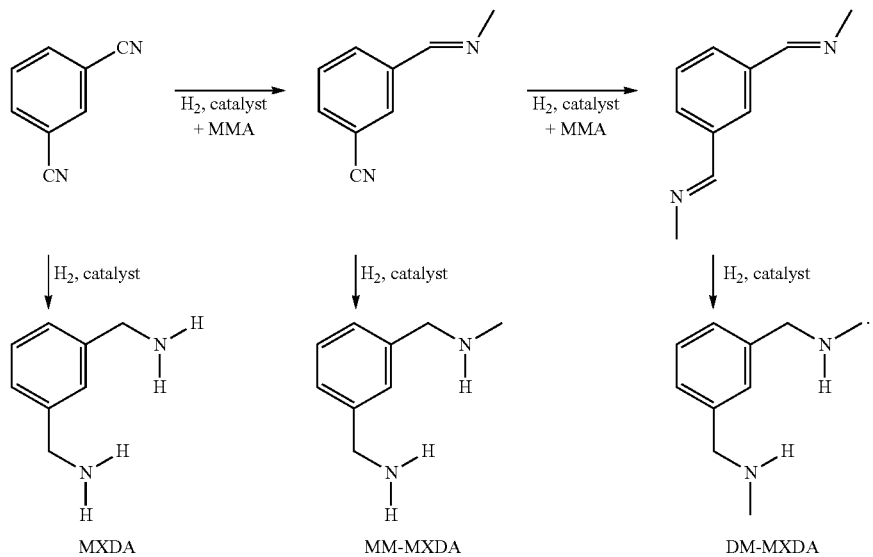

In this process, the at least one intermediate product of step (a) can comprise ammonia and unreacted mono-methylamine, and in yet another aspect of this invention, at least 50% by weight of the ammonia and unreacted mono-methylamine in the at least one intermediate product is removed prior to step (b). In other aspects of this invention, at least 70% by weight, at least 90% by weight, or substantially all, of the ammonia and unreacted methylamine can be removed prior to the second stage of the process.

Generally, the process for producing a mixture of amines comprising DM-MXDA produces at least about 60% yield by weight of DM-MXDA in the mixture of amines. In another aspect, the yield of DM-MXDA in the mixture of amines is at least about 70% by weight. Yet, in another aspect, the yield of DM-MXDA in the mixture of amines is at least about 75%, or at least about 80%, by weight.

In another aspect, the process for producing a mixture of amines comprising DM-MXDA produces very little, if any, meta-xylylenediamine (MXDA). Accordingly, MXDA can be present in the mixture of amines in an amount less than about 10% yield by weight. Often, the yield of MXDA in the mixture of amines is less than about 5%, or alternatively, less than about 3%, by weight.

Multifunctional Amine

Compositions in accordance with the present invention can comprise at least one multifunctional amine. Multifunctional amine, as used herein, describes compounds with amine functionality and which contain three (3) or more active amine hydrogens.

It can be beneficial to limit the volatility of the specific multifunctional amine used in some applications where worker exposure and safety issues may arise. Thus, in one aspect of the present invention, the at least one multifunctional amine contains 6 or more carbon atoms. In another aspect, the at least one multifunctional amine contains 8 or more carbon atoms. In yet another aspect, the at least one multifunctional amine contains 12 or more carbon atoms.

Non-limiting examples of multifunctional amines that are within the scope of the present invention include, but are not limited to, an aliphatic amine; a cycloaliphatic amine; an arene amine; an aromatic amine; a Mannich base derivative of an aliphatic amine, a cycloaliphatic amine, an arene amine, or an aromatic amine; a polyamide derivative of an aliphatic amine, a cycloaliphatic amine, an arene amine, or an aromatic amine; an amidoamine derivative of an aliphatic amine, a cycloaliphatic amine, an arene amine, or an aromatic amine; an amine adduct derivative of an aliphatic amine, a cycloaliphatic amine, an arene amine, or an aromatic amine; and the like; or any combination thereof.

More than one multifunctional amine can be used in the compositions of the present invention. For example, the at least one multifunctional amine can comprise an aliphatic amine and a Mannich base derivative of a cycloaliphatic amine. Also, the at least one multifunctional amine can comprise one aliphatic amine and one different aliphatic amine.

Exemplary aliphatic amines include polyethylene amines (triethylenetetramine, tetraethylenepentamine, pentaethylenehexamine and the like), 1,6-hexanediamine, 3,3,5-trimethyl-1,6-hexanediamine, 3,5,5-trimethyl-1,6-hexanediamine, 2-methyl-1,5-pentanediamine (commercially available as Dytek®-A), bis-(3-aminopropyl)amine, N,N'-bis-(3-aminopropyl)-1,2-ethanediamine, N,N-dimethyl-1,3-propyldiamine, N,N-ethyl-1,3-propyldiamine, aminoethylpiperazine, and the like, or combinations thereof. Additionally, the poly(alkylene oxide) diamines and triamines commercially available under the Jeffamine name from Huntsman Corporation, are useful in the present invention. Illustrative examples include, but are not limited to, Jeffamine® D-230, Jeffamine® D-400, Jeffamine® D-2000, Jeffamine® D-4000, Jeffamine® T-403, Jeffamine® EDR-148, Jeffamine® EDR-192, Jeffamine® C-346, Jeffamine® ED-600, Jeffamine® ED-900, Jeffamine® ED-2001, and the like, or combinations thereof.

Cycloaliphatic amines include, but are not limited to, 1,2-diaminocyclohexane, 1,3-diaminocyclohexane, 1,4-diaminocyclohexane, hydrogenated ortho-toluenediamine, hydrogenated meta-toluenediamine, isophorone diamine (IPDA), N-aminopropyl-cyclohexylamine (APCHA), hydrogenated metaxylylene diamine (referred to commercially as 1,3-BAC), various isomers of norbornane diamine, 3,3'-dimethyl-4,4'-diaminodicyclohexyl methane, 4,4'-diaminodicyclohexyl methane, 2,4'-diaminodicyclohexyl methane, and the like, or combinations thereof. Another cycloaliphatic amine is the mixture of methylene bridged poly(cyclohexyl-aromatic)amines, abbreviated as either MBPCAA or MPCA, and is described in U.S. Pat. No. 5,280,091, which is incorporated herein by reference in its entirety. In one aspect of the present invention, the at least one multifunctional amine is a mixture of methylene bridged poly(cyclohexyl-aromatic) amines (MPCA).

Illustrative and non-limiting examples of aromatic amines include ortho-toluenediamine, meta-toluenediamine, meta-phenylenediamine, a mixture of methylene bridged poly(phenylene) amines (e.g., a condensation product derived from aniline and formaldehyde), an isomeric mixture of 2,2'-/2,4'-/4,4'-diaminodiphenylmethane (often referred to as methylene dianiline or MDA), and the like, or combinations thereof.

Arene amines are distinguished from aromatic amines in that the nitrogen is attached directed to the aromatic ring in an aromatic amine, whereas for arene amines, the nitrogen is not attached directly to the aromatic ring. For instance, the nitrogen may be separated from the aromatic ring by a saturated or unsaturated alkyl. Examples of suitable arene amines include, but are not limited to, meta-xylylene diamine (MXDA), ortho-xylylene diamine, para-xylylene diamine, and the like, or combinations thereof. MM-MXDA is also an arene amine.

Mannich base derivatives suitable for use as a multifunctional amine can be made by the reaction of the above described aliphatic amines, cycloaliphatic amines, arene amines, or aromatic amines with phenol or a substituted phenol and formaldehyde. An exemplary substituted phenol used to make Mannich bases with utility in the present invention is cardanol, which is obtained from cashew nut shell liquid. Alternatively, Mannich bases can be prepared by an exchange reaction of a multifunctional amine with a tertiary amine containing a Mannich base, such as tris-(dimethylaminomethyl)phenol (commercially available as Ancamine® K54 from Air Products and Chemicals, Inc.) or bis-(dimethylaminomethyl)phenol. Additionally, it is contemplated that a Mannich base derivative of DM-MXDA can be employed. Such a material can be derived, for example, by reacting DM-MXDA with phenol (or a substituted phenol) and formaldehyde to produce a Mannich base curing agent with a low level of residual phenol (or substituted phenol). Polyamide derivatives can be prepared by the reaction of an aliphatic amine, cycloaliphatic amine, arene amine, or aromatic amine with dimer fatty acid, or mixtures of a dimer fatty acid and a fatty acid. Amidoamine derivatives can be prepared by the reaction of an aliphatic amine, cycloaliphatic amine, or aromatic amine with fatty acids. Amine adducts can be prepared by the reaction of an aliphatic amine, cycloaliphatic amine, arene amine, or aromatic amine with an epoxy resin, for example, with the diglycidyl ether of bisphenol-A, the diglycidyl ether of bisphenol-F, or epoxy novolac resins. The aliphatic, cycloaliphatic, arene, and aromatic amines also can be adducted with monofunctional epoxy resins, such as phenyl glycidyl ether, cresyl glycidyl ether, butyl glycidyl ether, other alkyl glycidyl ethers, and the like. These and other suitable amine derivatives are disclosed by W. R. Ashcroft, in "Curing Agents for Epoxy Resins," in B. Ellis, ed., Chemistry and Technology of Epoxy Resins (Blackie Academic and Professional, London, 1993), pp. 37-71, the disclosure of which is incorporated herein by reference.

Multifunctional Epoxy Resin

Amine-epoxy compositions of the present invention comprise an epoxy component, the epoxy component comprising at least one multifunctional epoxy resin. Multifunctional epoxy resin, as used herein, describes compounds containing 2 or more 1,2-epoxy groups per molecule. Epoxide compounds of this type are described in Y. Tanaka, "Synthesis and Characteristics of Epoxides", in C. A. May, ed., Epoxy Resins Chemistry and Technology (Marcel Dekker, 1988), which is incorporated herein by reference.

One class of epoxy resins suitable for use in the present invention comprise the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl)propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

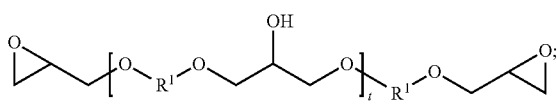

where t is an integer, and $R^1$ is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of the dihydric phenol and the dihydric phenol. While in any given molecule the value of t is an integer, the materials are invariably mixtures which can be characterized by an average value of t which is not necessarily a whole number. Polymeric materials with an average value of t between 0 and about 7 can be used in one aspect of the present invention.

In another aspect, epoxy novolac resins, which are the glycidyl ethers of novolac resins, can be used as multifunctional epoxy resins in accordance with the present invention. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products ranges from about 450 to 3000 or more. Because these products are solid at room temperature, they are often referred to as solid epoxy resins.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature.

Depending upon the end-use application, it can be beneficial to reduce the viscosity of the compositions of the present invention by modifying the epoxy component. For example, the viscosity can be reduced to allow an increase in the level of pigment in a formulation or composition while still permitting easy application, or to allow the use of a higher molecular weight epoxy resin. Thus, it is within the scope of the present invention for the epoxy component, which comprises at least one multifunctional epoxy resin, to further comprise a monofunctional epoxide. Examples of monoepoxides include, but are not limited to, styrene oxide, cyclohexene oxide, ethylene oxide, propylene oxide, butylene oxide, and the glycidyl ethers of phenol, cresols, tert-butylphenol, other alkyl phenols, butanol, 2-ethylhexanol, $C_4$ to $C_{14}$ alcohols, and the like.

Plasticizers and Solvents and Other Additives

Compositions of the present invention can be used to produce various articles of manufacture. Depending on the requirements during the manufacturing of or for the end-use application of the article, various additives can be employed in the formulations and compositions to tailor specific properties.

In some aspects of this invention, a plasticizer or solvent is added to the amine or amine-epoxy composition. Generally, suitable plasticizers or solvents can be aromatics, aliphatics, esters, ketones, ethers, alcohols, glycols, glycol ethers, and the like, and mixtures thereof. For example, ketones such as acetone, methyl ethyl ketone, methyl isoamyl ketone, methyl propyl ketone, methyl amyl ketone, diacetone alcohol, and the like, can be used as a solvent, often resulting in improved pot life with little or no sacrifice in drying speed. If ester plasticizers or solvents are included in the composition or formulation, such as esters of phthalic acid, it is usually necessary to formulate them in the package containing the epoxy resin, so as to minimize their reaction with the amine curing agent. Other useful plasticizers or solvents include, but are not limited to, benzyl alcohol, n-butanol, iso-propanol, toluene, xylene, nonyl phenol, dodecyl phenol, t-butyl phenol, bisphenol-A, cresol, cashew nutshell liquid, propylene glycol monomethyl ether (often abbreviated as PM), and aliphatic and/or aromatic hydrocarbon solvents such as those commercially available under the trademark name Shellsol. Mixtures of combinations of more than one plasticizer or solvent can be used. For example, the at least one plasticizer or solvent employed in amine or amine-epoxy compositions of this invention can comprise benzyl alcohol, n-butanol, xylene, methyl ethyl ketone, nonyl phenol, dodecyl phenol, cardanol, an ester of phthalic acid, or combinations thereof.

Other plasticizers which can be used in the accordance with this invention are well known to those skilled in the art, and are described more extensively in D. F. Cadogan and C. J. Howick, 'Plasticizers', in J. I. Kroschwitz, ed., Kirk-Othmer Encyclopedia of Chemical Technology, 4th Ed., Wiley, New York, 1996, Vol. 19, pp. 258-290. Plasticizers in epoxy-amine thermosetting coatings are typically utilized in systems that are cured at ambient or sub-ambient temperatures. Upon applying a heat cure, even a mild one, substantial emissions of plasticizer may occur, often leading to film shrinkage and stress build-up. This is contrasted with adhesive applications, where the ability to adjust the adhered parts by applying additional heat, typically ranging between about 50 and about 160° C., following the initial cure at ambient temperature can be important.

Other additives that can be employed in the compositions and formulations of this invention include, but are not limited to, accelerators, fillers, fibers such as glass or carbon fibers, pigments, pigment dispersing agents, rheology modifiers, thixotropes, flow or leveling aids, defoamers, or any combination thereof. It is understood that other mixtures or materials that are known in the art can be included in the compositions or formulations and are within the scope of the present invention.

In some circumstances, it may be advantageous to employ accelerators for the epoxy-amine curing reaction. Such accelerators are described in H. Lee and K. Neville, *Handbook of Epoxy Resins*, McGraw-Hill, New York, 1967. One of skill in the art would recognize that some of the aforementioned plasticizers or solvents can also serve as accelerators. Additional non-limiting examples of accelerators include various organic acids, tertiary amines, and hydroxylamines, such as, for example, salicylic acid, dimethylaminomethylphenol, bis(dimethylaminomethyl)phenol, tris(dimethylaminomethyl) phenol, and the like, or combinations thereof. Normally, accelerators are used at levels of 10% or less based on the total weight of binder, and more often at levels of 5% or less.

Further, compositions within the scope of the present invention can be solventless, also referred to as solvent-free or 100% solids. Alternatively, these compositions can further comprise at least one solvent (a solvent is also referred to as a diluent). Often, a solvent or mixture of solvents is chosen to give a specific evaporation rate profile for the composition or formulation, while maintaining solubility of the components of the formulation.

Articles

The present invention also is directed to articles of manufacture comprising the compositions disclosed herein. For example, an article can comprise a cured amine-epoxy composition which comprises the contact product of an amine curing agent component and an epoxy component. The amine curing agent component can comprise DM-MXDA and at least one multifunctional amine. The epoxy component can comprise at least one multifunctional epoxy resin. Optionally, various additives can be present in the compositions or formulations used to produce fabricated articles, dependent upon the desired properties. These additives can include, but are not limited to, plasticizers or solvents, accelerators, fillers, fibers such as glass or carbon fibers, pigments, pigment dispersing agents, rheology modifiers, thixotropes, flow or leveling aids, defoamers, or any combination thereof.

Articles in accordance with the present invention include, but are not limited to, a coating, a construction product, a flooring product, or a composite product. Coatings based on these amine-epoxy compositions can be solvent-free or can contain solvents as needed for the particular application. For example, coatings with solids content greater than 50%, greater than 65%, greater than 75%, or greater than 85%, are within the scope of the present invention. Coatings can contain various types and levels of pigments for use in paint applications.

Numerous substrates are suitable for the application of coatings of this invention with proper surface preparation, as is well known to one of ordinary skill in the art. Such substrates include, but are not limited to, cementitious materials such as concrete and various types of metals and alloys, such as steel and aluminum. For example, the low temperature cure, good surface appearance when applied at room temperature, good flexibility properties, and good corrosion protection of the coatings of the present invention make them suitable for the painting or coating of large metal objects or cementitious substrates which must be painted and/or cured at room temperature or colder conditions, including ships, bridges, industrial plants and equipment, and floors. Coatings of this invention can be applied and cured at temperatures ranging from about $-10°$ C. to about $50°$ C., or alternatively, at temperatures ranging from about $0°$ C. to about $35°$ C. As needed, these coatings also can be force cured at higher temperatures, which often can improve the flexibility of the cured material. Accordingly, objects coated with amine-epoxy compositions of the present invention, especially large metal objects which are often painted and cured under ambient conditions, or sub-ambient conditions, including ships, bridges, and industrial plants, and equipment, are contemplated and encompassed by the present invention.

Coatings in accordance with the present invention typically have a thickness between 50 and 5,000 μm depending on the type of application and the targeted substrate. For example, coatings applied to metal, concrete, or cementitious substrates for the purpose of protecting that substrate against mechanical and/or chemical stress often have a thickness between about 50 and about 500 μm, or between about 100 and about 300 μm. Alternatively, coatings or formulations that are required to provide load bearing properties to the substrate underneath, such as those illustrated in Examples 32-36 that follow typically have a thickness of around 1 to 3 millimeters.

Coatings differ from adhesives in several ways. For instance, an adhesive is designed to establish adhesion between two substrates or surfaces and keep those substrates or surfaces adhered together. Consequently, there is generally limited to no direct exposure of the adhesive to the environment. A coating, in contrast, adheres to one substrate or surface. Thus, the surface of the coating that faces away from the adhering substrate or surface (the "coating surface") is exposed to the environment, which can be air, other gases, water/humidity, chemicals, etc. The coating surface also provides an aesthetic finish which can be characterized by the degree of gloss and the ability to resist carbamation. The properties of the coating surface also impact its ability to resist mechanical, chemical, or thermal exposures and, as such, directly impact its ability to protect the substrate or surface underneath. Analytical tests that can be used to assess these properties include EIS resistance data, impact resistance, mandrel bend, Persoz pendulum hardness, and so forth. For example, coatings of the present invention generally have 24-hour EIS pore resistance values of at least about $1 \times 10^7 \Omega$. In another aspect, a coating of the present invention has a 24-hour EIS pore resistance value of at least about $1 \times 10^8 \Omega$. Yet, in another aspect, a coating of the present invention has a 24-hour EIS pore resistance value of at least about $1 \times 10^9 \Omega$.

In another aspect, for example, in construction applications, a coating of the present invention can be characterized by having an impact resistance (direct; Schedule A) in a range from about 30 to about 200 kg.cm. For instance, the impact resistance can be in a range from about 40 to about 100, or from about 45 to about 70 kg.cm.

Coatings also differ from adhesives in their ability to cure rapidly at ambient temperature or at sub-ambient temperature. For example, coatings applied in shipyards can be required to cure at 5° C. or even lower, since shipyards are often located in climates with cold winters and ships or parts of ships cannot be heated to facilitate higher temperature conditions. Curing at low temperatures is also pertinent for construction flooring applications where coatings are applied in parking areas and warehouses under sub-ambient conditions, or in buildings where rapid back-in-service times are required to minimize closure of the area to public. Cure or drying times can be assessed using a measurement such as thin film set time, as well as Persoz pendulum hardness. Generally, coatings of the present invention have thin film set times at 25° C. (Phase 2 and/or Phase 3) of less than about 12 hours, for example, less than about 8 hours, or less than about 6 hours. Furthermore, coatings of this invention can be characterized as having a thin film set time in a range from about 1 hour to about 8 hours, or from about 1 hour to about 6 hours in other aspects of this invention. For instance, the thin film set time of a coating of the present invention can be in a range from about 1 to about 5 hours at 25° C.

Likewise, it is contemplated that coatings of the present invention can have thin film set times at 5° C. (Phase 2 and/or Phase 3) of less than about 25 hours, for example, less than about 20 hours. Often, the thin film set time is in a range from about 2 to about 18 hours, or from about 2 to about 15 hours, at 5° C. In some aspects of this invention, the thin film set time of the coating at 5° C. is in a range from about 2 to about 12 hours, or from about 2 to about 10 hours.

Coatings of this invention can be applied by any number of techniques including spray, brush, roller, paint mitt, and the like. In order to apply very high solids content or 100% solids coatings of this invention, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Civil engineering end-uses can comprise construction and flooring applications, including formulations comprising the amine-epoxy compositions of the present invention in combination with cementitious materials such as concrete, or other materials commonly used in the construction industry. Compositions of the present invention can be used in the construction of epoxy-based floors, often in applications requiring better mechanical properties (e.g., improved tensile strength or improved compressive strength) or better elongation than that normally obtained from cementitious or other similar types of flooring materials. Crack injection and crack filling products also can be prepared from the compositions disclosed herein, as well as polymer modified cements, tile grouts, mortars, and the like. Products for concrete and cementitious materials employing amine-epoxy compositions, such as floor primers and coatings ranging in thickness from the tens of microns up to several millimeters thick, are also contemplated herein.

Non-limiting examples of composite products or articles comprising amine-epoxy compositions disclosed herein include tennis rackets, skis, bike frames, airplane wings, glass fiber reinforced composites, and other molded products.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Coatings of amine-epoxy compositions were prepared and tested as follows. Hardener mixtures or compositions, including amine compositions in accordance with the present invention, were prepared by contacting and mixing the components given in the tables that follow. The respective hardener mixture or composition, or the individual hardener, was then mixed with a multifunctional epoxy resin at the use level indicated in the tables in parts per hundred weight resin (PHR). The epoxy resin used in these examples, unless specified otherwise, was the diglycidyl ether of bisphenol-A (DGEBA), grade D.E.R.™ 331 with an EEW in the range of 182 to 192. This epoxy resin is commercially available from the Dow Chemical Company.

Coating properties were measured in accordance with the standard test methods listed in Table 1. Clear coatings were applied to standard glass panels to produce samples for drying time testing using a Beck-Koller drying time recorder and for hardness development by the Persoz pendulum hardness method. Clear coatings for specular gloss were applied to uncoated, matte paper charts (AG5350, Byk). Coatings were applied at 75 micron WFT (wet film thickness) using a Bird applicator resulting dry film thicknesses from 60 to 70 microns. Films were cured at 5° C. and 60% RH (relative humidity) or 25° C. and 60% RH using a Weiss climate chamber (type WEKK0057). Shore A and Shore D data were recorded at 3 sec after positioning the device onto 2 mm thick epoxy castings, which were cured at approximately 23° C. and 60% RH. Persoz hardness and Shore A and Shore D data were measured at the times indicated in the tables.

Clear coatings for impact resistance and mandrel bend testing were applied to respectively cold-rolled steel test panels, ground one side (approximate size 76 mm×152 mm×0.8 mm thick) and cold-rolled steel, smooth finish (approximate size 76 mm×152 mm×0.5 mm thick), using a nominal 75 WFT wire bar. Metal test panels were obtained from Q Panel Lab Products. Films were cured according to the following schedules: (A) 14 days ambient temperature, ambient temperature being approximately 23° C.; or (B) 14 days ambient temperature followed by 2 hours at 80° C. Dry film thicknesses were from about 60 to 80 microns following cure schedule A, and from about 50 to 55 microns following schedule B.

Mix viscosities were determined using a Rheolab MC20 apparatus (Physica) equipped with a Viscotherm VT10 water bath and MC20 temperature control unit. The equipment was set up with the TEK 150 cone-plate and connected to a computer. After the apparatus was equilibrated at 25° C., the gap between the cone (MK22) and plate was set to approximately 50 µm. Samples were equilibrated at 25° C. for 24 hours before testing. After mixing as indicated, excess product running out of the gap was removed and the rotational viscosity of the mixed product was recorded at a 200 reciprocal second shear rate after 30 seconds.

Clear coatings for electrochemical impedance spectroscopy (EIS) measurements were applied to cold-rolled steel test panels, ground one side (approximate size 76 mm×152 mm×0.8 mm thick). Coatings were applied using a 75 micron WFT wire bar to result in film thicknesses between 60 and 70 microns following a 7-day cure at 23° C. and 60% RH. EIS was conducted using a FAS1 potentiostat with CMS100 Electrochemical Measurement System (Gamry Instruments, Inc.). The coating surface exposed to the electrolyte (3 wt %

NaCl solution) was reduced to a 1 cm² circle by applying a plastic sticker. Using a graphite rod electrode, resistance and capacitance data of the coating were collected against a saturated calomel electrode (SCE) during 100 sec by applying a 10 mV AC excitation voltage. Following Fourier transformation, resistance was plotted as a function of frequency, and impedance data was analyzed and fitted to result in pore resistance data. Water uptake (V in wt %) was calculated from the change in capacitance between 1 hour ($R_{c(1h)}$) and 24 hour ($R_{c(24h)}$) exposure, using expression, V=100*[log {$R_{c(1h)}$/$R_{c(24h)}$}/log 80].

Gelation time or gel-time was recorded as the time after mixing the epoxy resin and the amine-based hardener to reach a defined point of viscosity as determined using a Techne GT3 Gelation Timer, equipped with disposal glass plungers (13 mm in diameter) and operating at one cycle per minute. Samples were equilibrated for 24 hr at room temperature before use. Gelation time was recorded for a 100 g amine-epoxy mixture charged to 100-ml glass jar, reacting at ambient temperature conditions (approximately 23° C.). Flow characteristics of the homogeneous mixture of epoxy resin and the amine-based hardener was determined by pouring 30 g of the mixture onto a horizontal substrate. After the mixture had cured, the diameter of flow was recorded in millimeters.

TABLE 1

Analytical test methods.

| Property | Response | Test Method |
| --- | --- | --- |
| Drying Time: Beck-Koller Recorder | Thin film set times, phases 2 & 3 (hr) | ASTM D5895 |
| Specular Gloss | Gloss at 20° and 60° | ISO 2813, ASTM D523 |
| Persoz Pendulum Hardness | Persoz hardness (s) | ISO 1522, ASTM D4366 |
| Shore A & D Hardness | Shore A or D | ISO 868, ASTM D2240 |
| Impact Resistance - Tubular Impact Tester | Direct and reverse impact (kg.cm) | ISO 6272, ASTM D2794 |
| Mandrel Bend Test: Cylindrical Bend | Elongation (%) | ISO 1519, ASTM D1737 |
| Mandrel Bend Test: Conical Bend | Elongation (%) | ISO 6860, ASTM D522 |

Comparative Examples 1-2

Synthesis of a Mixture of Amines Containing DM-MXDA Using a One Stage Process

In Example 1, 50 g of tetrahydrofuran (THF), 20 g of 1,3 dicyanobenzene, and 0.2 g of 5% Pd/C catalyst were placed in a 250-ml stainless-steel batch pressure reactor equipped with a stirrer and a hydrogen ballast tank. The Pd/C catalyst is commercially available from the Johnson-Mathey Corporation. The reactor was purged with nitrogen. and sealed. While stirring the reactor contents, 36 g of methylamine (MMA) were added to the reactor. The reactor was then pressurized with hydrogen to 800 psi (5.5 MPa), and heated to 120° C. These conditions were maintained until the rate of hydrogen uptake from the ballast tank fell below 0.5 psi/min (0.0034 MPa/min). The reactor was cooled to room temperature and depressurized, and the product was filtered to remove the catalyst. The reaction product of Example 1 contained a mixture of amines, predominantly MXDA with only small amounts of MM-MXDA and DM-MXDA.

Example 2 employed the same reactant materials as in Example 1, except that 0.2 g of a 5% Ru/Al₂O₃ catalyst were used. This catalyst is commercially available from BASF. While stirring, the reaction was allowed to proceed for 1000 minutes at a constant pressure of 375 psi (2.6 MPa) and a temperature of 125° C. After filtration to remove the catalyst, the reaction product of Example 2 contained a mixture of amines. Table 2 demonstrates that Example 2 yielded 44.9% MXDA and 54.9% heavies, but no DM-MXDA or MM-MXDA. Examples 1-2 are not effective processes for synthesizing DM-MXDA.

Examples 3-4

Synthesis of a Mixture of Amines Containing DM-MXDA Using a Two Stage Process

Tables 2-3 summarize the reaction conditions and materials utilized in Examples 3 and 4, as well as an analysis of the intermediate and final reaction products. In Example 3, 50 g of THF, 20 g of 1,3 dicyanobenzene, and 0.2 g of 5% Pd/C catalyst were placed in a 250-ml stainless-steel batch pressure reactor equipped with a stirrer and a hydrogen ballast tank. The reactor was purged with nitrogen and sealed. While stirring the reactor contents, 34 g of methylamine (MMA) were added to the reactor. The reactor was then pressurized with hydrogen to 375 psi (2.6 MPa) and heated to 125° C. These reaction conditions were maintained for 1000 minutes, then the reactor was cooled to room temperature and depressurized.

As shown in Table 2, the resultant intermediate product (first stage product) was high in imine content. In the second stage of the process, the intermediate product was hydrogenated at 125° C. and 800 psi (5.5 MPa) for 150 minutes using the same catalyst employed in the first stage of the process. Table 2 shows that the final amine reaction product of Example 3 contained approximately 45% MM-MXDA and 35% DM-MXDA.

Example 4 employed substantially the same procedure as that of Example 3. A 5% Raney Nickel catalyst, commercially available from WR Grace, was used in Example 4. The final amine mixture contained about 15% DM-MXDA. Further details are provided in Tables 2-3.

In comparison to Examples 1-2, Examples 3-4 demonstrated the importance of conducting a two-step process if DM-MXDA or MM-MXDA is the desired product. Examples 3-4 demonstrated a significant reduction in the yield of MXDA in comparison to that found in amine product of Example 2.

Examples 5-6

Synthesis of a Mixture of Amines Containing DM-MXDA Using a Two Stage Process

Tables 2-3 summarize the reaction conditions and materials utilized in Examples 5 and 6, as well as an analysis of the intermediate and final reaction products. Example 5 employed substantially the same procedure as that of Example 3. A 5% Rh/Al₂O₃ catalyst, commercially available from BASF, was used in Example 5. At the end of the first stage, the composition of the intermediate reaction product contained 73% of the respective di-imine. The Rh/Al$_2$O$_3$ catalyst was removed by filtration, and a 5% Pd/C catalyst was used for the hydrogenation step. The resulting mixture of amines had a very high yield of DM-MXDA (73%) with about 15% MM-MXDA. Further details are provided in Tables 2-3.

Example 6 employed substantially the same procedure as that of Example 5. In the second step of the process, a Raney Nickel catalyst was employed as the hydrogenation catalyst. The final amine reaction product contained 61% DM-MXDA and 26% MM-MXDA. Further details are provided in Tables 2-3.

As compared to Examples 3-4, Examples 5-6 produced much higher levels of the respective di-imine in the intermediate reaction product of the first stage of the process. Further, the final amine products of Examples 5-6 contained higher amounts of DM-MXDA with lower amounts of MM-MXDA. While not intending to be bound by theory, it appears that increasing the amount of di-imine or the amount of the adduct between MMA and 1,3-dicyanobenzene produced in the first stage will increase the yield of DM-MXDA produced in the second stage.

Examples 7-8

Synthesis of a Mixture of Amines Containing DM-MXDA Using a Two Stage Process

Tables 2-3 summarize the reaction conditions and materials utilized in Examples 7 and 8, as well as an analysis of the final reaction product. Example 7 illustrated a one-pot process, using 10% Pd/C as a catalyst. The 10% Pd/C catalyst is commercially available from the Johnson-Mathey Corporation. The process of Example 7 was conducted in two steps, where the aminomethylation and the hydrogenation were done in-situ as a batch reaction.

In the first step, 200 g of 1,3-dicyanobenzene, 3 g of 10% Pd/C catalyst, and 200 g of THF were are placed in a 1000-cc Parr pressure reactor. The reactor was sealed and pressure cycled 3 times with nitrogen to remove the air, and then 3 times with hydrogen to remove the nitrogen. While stirring the reactor contents at 300 rpm, 185 g of anhydrous MMA were added to the sealed reactor under 1 atmosphere of hydrogen pressure. Once the addition was complete, the reactor contents were heated to 80° C. and maintained at a hydrogen pressure of about 325 psi, while stirring at 1000 rpm. These conditions were maintained until the rate of hydrogen uptake fell below 1 psi/min (0.0069 MPa/min) from a 1-liter ballast tank. The reactor was then cooled to the 50-60° C. range, and the excess MMA and ammonia were slowly vented from the intermediate reaction product.

In the second step of the process, the temperature was increased to about 130° C., and the hydrogen pressure was increased to 950 psi. These conditions were maintained until the rate of hydrogen uptake fell below about 0.5 psi/min. The reactor was then held at these conditions for one additional hour. The total hydrogenation reaction time was approximately 300 minutes. The reactor contents were then cooled to room temperature, filtered to remove the catalyst, and roto-evaporated to remove the solvent and any light components. The composition of the final amine product of Example 7 is reported in Table 3.

Example 8 employed substantially the same procedure as that of Example 7. Example 8 utilized 6 g of a 5% Pd/C catalyst. Further details are provided in Tables 2-3.

As shown in Table 3, the processes of Examples 7-8 resulted in yields of DM-MXDA in the final mixtures of amines that were in excess of 70%, while producing very low amounts of by-products such as MXDA or the imine derivatives. Both Examples 7-8 employed the step of venting the reactor at the end of the first stage to allow removal of unreacted MMA and ammonia. Further, Examples 7-8 used the same catalyst in both stages of the reaction, thus eliminating the need for a separate filtration step after the first stage of the reaction.

TABLE 2

Summary of reaction of 1,3-dicyanobenzene with MMA for Examples 2-8.

| | Example | | | | | | |
|---|---|---|---|---|---|---|---|
| | 2 | 3 | 4 | 5 | 6 | 7 | 8 |
| 1,3-dicyanobenzene (g) | 20 | 20 | 20 | 20 | 20 | 200 | 200 |
| MMA (g) | 36 | 34 | 36 | 36 | 36 | 185 | 200 |
| Catalyst amount (g) | 0.2 | 0.2 | 0.2 | 0.2 | 0.2 | 3.0 | 6.0 |
| Catalyst type | 5% Rh/Al$_2$O$_3$ | 5% Pd/C | Raney Nickel | 5% Rh/Al$_2$O$_3$ | 5% Rh/Al$_2$O$_3$ | 10% Pd/C | 5% Pd/C |
| Reaction Time (min) | 1000 | 1000 | 1000 | 920 | 900 | 360 | 300 |
| Temperature (° C.) | 125 | 125 | 125 | 125 | 125 | 80 | 80 |
| Pressure (psi) | 375 | 375 | 375 | 375 | 375 | 325 | 325 |
| First Stage Product (%) | | | | | | 100[a] | 100[a] |
| MXDA | 44.9 | 0 | 7.0 | 1.0 | 0.9 | | |
| MM-MXDA | 0 | 0.2 | 2.6 | 0 | 0 | | |
| DM-MXDA | 0 | 0.9 | 2.3 | 0.5 | 1.4 | | |
| Mono-Imine | 0 | 81.8 | 14.3 | 0 | 0.6 | | |
| Di-Imine | 0.2 | 0.2 | 45.3 | 73.1 | 71.9 | | |
| Heavies + Other | 54.9 | 2.5 | 20.5 | 20.1 | 21.7 | | |

[a]Composition of intermediate product of the first stage was not determined.

TABLE 3

Summary of hydrogenation reaction for Examples 3-8.

| | Example | | | | | |
|---|---|---|---|---|---|---|
| | 3 | 4 | 5 | 6 | 7 | 8 |
| Catalyst amount (g) | 0.2 | 0.2 | 0.2 | 0.5 | 3.0 | 6.0 |
| Catalyst type | 5% Pd/C[a] | Raney Nickel[a] | 5% Pd/C | Raney Nickel | 10% Pd/C[a] | 5% Pd/C[a] |
| Reaction Time (min) | 150 | 180 | 60 | 90 | 300 | 360 |

TABLE 3-continued

Summary of hydrogenation reaction for Examples 3-8.

|  | Example | | | | | |
|---|---|---|---|---|---|---|
|  | 3 | 4 | 5 | 6 | 7 | 8 |
| Temperature (° C.) | 125 | 125 | 100 | 150 | 130 | 130 |
| Pressure (psi[a]) | 800 | 375 | 800 | 800 | 950 | 975 |
| Composition (%) | | | | | | |
| MXDA | 3.1 | 9.5 | 0 | 2.3 | 1.9 | 0.9 |
| MM-MXDA | 44.7 | 41.3 | 15.3 | 26.1 | 9.7 | 8.2 |
| DM-MXDA | 34.8 | 14.5 | 72.8 | 61.2 | 72.0 | 81.5 |
| Mono-Imine | 0 | 0 | 0.6 | 1.0 | 0.8 | 0.2 |
| Di-Imine | 0 | 9.4 | 5.5 | 0.3 | 0.7 | 1.5 |
| Heavies + Other | 13.8 | 16.8 | 3.8 | 7.2 | 14.6 | 7.7 |

[a]Catalyst from first stage of the process; no new catalyst added.

Example 9

Synthesis of a Mixture of Amines Containing DM-MXDA Using a Two Stage Process 200 g of THF, 200 g of 1,3 dicyanobenzene, and 3 g of 10% Pd/C catalyst were placed in a 1-liter stainless-steel batch pressure reactor equipped with a stirrer and a 1-liter hydrogen ballast tank. The reactor was purged with nitrogen and sealed. While stirring the reactor contents, 200 g of methylamine were added to the reactor. The reactor was then pressurized with hydrogen to 350 psi (2.4 MPa) and heated to 80° C. These conditions were maintained until the rate of hydrogen uptake from the ballast tank fell below 0.5 psi/min. The reactor was vented to remove ammonia and any unreacted MMA.

Then, the hydrogen reactor pressure was increased to 850 psi and the temperature was increased to the 125-130° C. range. These conditions were maintained until the rate of hydrogen uptake from the ballast tank fell below 0.5 psi/min. The reactor was then cooled to room temperature and depressurized, and the product was filtered to remove the catalyst. The reaction product was distilled under vacuum to yield an amine mixture containing 87.8% DM-MXDA and 11.7% MM-MXDA, as measured by gas chromatography via area percentages. In the tables that follow, this amine composition of Example 9 is designated as EX-9.

Comparative Examples 10-18

Coatings Made from Comparative Epoxy-Hardener Compositions

Formulations and the resulting properties of Comparative Examples 10-18 are summarized in Tables 4-5. Example 10 used a polyamide adduct curing agent which was high in viscosity and, therefore, had low solids at application viscosity. The coating of Example 10 exhibited slow dry speed and low hardness development at room temperature, and particularly at 5° C. The coating of Example 10 had good impact resistance.

Example 11 used an aliphatic amine curing agent which was also high in viscosity and, therefore, had low solids at application viscosity. The coating of Example 11 showed moderate impact resistance, but demonstrated fast cure speed and high gloss at ambient conditions and at 5° C.

Example 12 used a phenalkamine Mannich base, which was high in neat viscosity and, therefore, had low solids at application viscosity. This coating demonstrated slow dry speed and poor hardness development at 5° C. Additionally, the coating of Example 12 showed moderate impact and mandrel bend flexibility.

Example 13 illustrates coating properties using a multifunctional amine, such as MPCA, without DM-DMDA of the present invention. The coating composition had a high mix viscosity, the coating cured slowly at both ambient conditions and at 5° C., and the coating had poor impact resistance. The coating of Example 13 exhibited high gloss at both ambient temperature and at 5° C.

Example 14 used methylamine-terminated poly-(N-methylazacycloheptane) as a curing agent. This material can be produced in accordance with a procedure described in U.S. patent application Ser. No. 11/584,388, the disclosure of which is incorporated herein by reference in its entirety. The curing agent used in Example 14 was DSD-1 from U.S. patent application Ser. No. 11/584,388, having an estimated amine hydrogen equivalent weight (AHEW) of about 121 and a number-average molecular weight ($M_n$) of approximately 184. The coating of Example 14 exhibited fast dry speed at ambient temperature and excellent impact resistance. At 5° C., the coating showed moderate drying speed and was tacky.

Example 15 used a Mannich base derivative of methylamine-terminated poly-(N-methylazetidine) as a curing agent. This material can be produced in accordance with a procedure described in U.S. patent application Ser. No. 12/100,096, the disclosure of which is incorporated herein by reference in its entirety. The curing agent used in Example 15 was MBC-9 from U.S. patent application Ser. No. 12/100,096, having a viscosity of 59 mPa·s at 25° C. and an amine value of 850 mg KOH/g. The coating of Example 15 cured rapidly at ambient temperature and at 5° C., resulting in a high gloss coating with excellent flexibility.

Example 16 used methylamine-terminated poly-(N-methylazetidine) as a curing agent. This material can be produced in accordance with a procedure described in U.S. patent application Ser. No. 11/584,388. The curing agent used in Example 16 was DSD-4 from U.S. patent application Ser. No. 11/584,388, having an estimated AHEW of about 117, an amine value of 877 mg KOH/g, and a $M_n$ of approximately 239. As compared to Example 12, the coating formulation of Example 16 demonstrated lower mix viscosity, and resulted in coatings with improved flexibility and faster cure speed.

Example 17 used a Mannich base derivative of methylamine-terminated poly-(N-methylazetidine) as a curing agent. This material can be produced in accordance with a procedure described in U.S. patent application Ser. No.12/100,096. The curing agent used in Example 17 was MBC-9 from U.S. patent application Ser. No. 12/100,096, having a viscosity of 59 mPa·s at 25° C. and an amine value of 850 mg KOH/g. As compared to Example 12, the coating formulation of Example 17 demonstrated lower mix viscosity, and results in coatings with improved impact resistance and faster cure speed.

Example 18 used N,N'-dimethyl-1,6-hexamethylenediamine (DM-HMDA) with MPCA as a curing agent. This coating formulation had low viscosity and the respective coating exhibited fast dry speed and high impact resistance.

Coatings based on Examples 10-12 are often used in metal protection applications due to their moderate to high corrosion protection properties. These barrier properties are demonstrated by both the high pore resistance and the low water uptake data determined by EIS measurements. As shown in Table 4, the coating of Example 13 also provides high pore resistance and low water uptake. The combined properties of high pore resistance and low water uptake are desirable for obtaining good corrosion protection and to prevent early coating failure due to corrosion when the coatings are applied to metal substrates. The coatings of Examples 10-13 provide corrosion protection performance that is superior to that of the coatings of Examples 14-18.

TABLE 4

Comparative examples cured at 25° C. or following cure schedules A-B.

| | Example | | | |
|---|---|---|---|---|
| | 10 | 11 | 12 | 13 |
| Comparative Hardener | A2050 | A2603 | CX-105 | MPCA 100 / BA 43 |
| Use Level (PHR) | 80 | 90 | 76 | 42 |
| Mix viscosity (MPa · s) | 6,500 | 4,000 | 22,000 | 14,600 |
| Coating Solids (weight %) | | | | |
| At mix viscosity | 87 | 81 | 100 | — |
| Diluted to 1 Pa · s$^a$ | — | 76 | 87 | 91 |
| Thin Film Set Time (h) | | | | |
| Phase 2/Phase 3 | 7.5/>12 | 1.7/3.0 | —/— | 5.8/7.1 |
| Coating Appearance | | | | |
| Specular Gloss 20°/60° | 100/101 | 97/101 | 10/50 | 103/103 |
| Visual | high gloss | high gloss | semi gloss | high gloss |
| Persoz Hardness (s) | | | | |
| Day 1/Day 7 | 25/270 | 235/340 | 90/190 | 255/340 |
| Impact Resistance (kg · cm) Direct/Reverse | | | | |
| Schedule A | 150/30 | 65/6 | 85/17 | 40/<5 |
| Schedule B | >200/60 | 80/10 | | 90/60 |
| Mandrel Bend (% elongat.) | | | | |
| Schedule B | 6.5 | 4.1 | 5.3 | — |
| EIS Resistance Data | | | | |
| Pore Resistance, 24 h (Ω) | $2 \times 10^{10}$ | $7 \times 10^9$ | $2 \times 10^{10}$ | $1 \times 10^{10}$ |
| Water Uptake, 24 h (wt %) | 1.2 | 1.3 | 1.0 | <1 |

| | Example | | | | |
|---|---|---|---|---|---|
| | 14 | 15 | 16 | 17 | 18 |
| Comparative Hardener | DSD-1 78 / MPCA BA 43 | MBC-9 75 / MPCA BA 42 | DSD-4 50 / CX105 50 / BA 22 | MBC-9 50 / CX105 50 | DM-HMDA 68 / MPCA BA 32 43 |
| Use Level (PHR) | 76 | 86 | 80 | 83 | 50 |
| Mix viscosity (MPa · s) | — | 1,900 | 3,700 | 8,800 | 810 |
| Coating Solids (weight %) | | | | | |
| At mix viscosity | 87 | 86 | 92 | 100 | 90 |
| Diluted to 1 Pa · s$^a$ | — | — | 91 | — | — |
| Thin Film Set Time (h) | | | | | |
| Phase 2/Phase 3 | 2.8/3.5 | —/— | —/— | —/— | 3.0/3.6 |
| Coating Appearance | | | | | |
| Specular Gloss 20°/60° | 97/98 | >95 | >90 | >95 | 101/101 |
| Visual | high gloss | high gloss | glossy | high gloss | high gloss |
| Persoz Hardness (s) | | | | | |
| Day 1/Day 7 | 185/200 | 280/285 | 245/265 | 315/325 | 250/330 |
| Impact Resistance (kg · cm) Direct/Reverse | | | | | |
| Schedule A | >200/>200 | 170/85 | 200/65 | 140/35 | 130/40 |
| Schedule B | >200/>200 | —/— | —/— | —/— | >200/100 |
| Mandrel Bend (% elongat.) | | | | | |
| Schedule B | — | 33 | 33 | 5.3 | 5.2 |
| EIS Resistance Data | | | | | |
| Pore Resistance, 24 h (Ω) | $<1 \times 10^3$ | $<1 \times 10^3$ | $<1 \times 10^3$ | $2 \times 10^5$ | $3 \times 10^5$ |
| Water Uptake, 24 h (wt %) | >100 | >100 | >100 | >100 | 50 |

$^a$Adjusted with xylene:butanol (3:1) to match comparable application viscosity of 1 Pa · s.

TABLE 5

Comparative examples cured at 5° C.

|  | Example | | | |
|---|---|---|---|---|
|  | 10 | 11 | 12 | 13 |
| Thin Film Set Time (h) | | | | |
| Phase 2/Phase 3 | >48/>48 | 6.7/15 | 9.7/15.2 | 18.1/21.4 |
| Coating Appearance | | | | |
| Specular Gloss 20°/60° | —/— | 96/101 | 12/34 | 98/100 |
| Visual | tacky | high gloss | matte | high gloss |
| Persoz Hardness (s) | | | | |
| Day 2/Day 7 | —/85 | 25/200 | 25/75 | 11/140 |

|  | Example | | | | |
|---|---|---|---|---|---|
|  | 14 | 15 | 16 | 17 | 18 |
| Thin Film Set Time (h) | | | | | |
| Phase 2/Phase 3 | 10.9/14.3 | 6.5/9.0 | 6.4/11.0 | 9.0/12.6 | 8.4/10.4 |
| Coating Appearance | | | | | |
| Specular Gloss 20°/60° | 15/55 | 97/100 | 86/95 | 81/94 | 50/70 |
| Visual | tacky | high gloss | glossy | glossy | mild carbamate |
| Persoz Hardness (s) | | | | | |
| Day 2/Day 7 | —/— | 75/180 | 95/210 | 135/250 | 90/135 |

Examples 19-30

Coatings Made from Amine-Epoxy Compositions

Formulations and the resulting properties of Examples 19-30 are shown in Tables 6-7. Examples 19-22 and 24-28 illustrate the properties obtained from exemplary formulations and coatings utilizing DM-MXDA in accordance with aspects of the present invention. These examples utilized the amine mixture of Example 9 (EX-9), containing approximately 87.8% DM-MXDA and 11.7% MM-MXDA. Example 23 illustrates the coating properties achieved by using a multifunctional amine, MXDA, without any DM-MXDA of the present invention. Examples 29-30 illustrate coating properties obtained using a cyclohexyl-TMD amine composition, abbreviated TMD-1 in Table 6, and with TMD being an abbreviation for 2,2,4(2,4,4)-trimethyl-hexamethylene-1,6-diamine. This TMD-1 amine mixture contained 74% N-cyclohexyl-TMD, 22% N,N'-dicyclohexyl-TMD, and 4% TMD, by weight.

The TMD-1 amine mixture was prepared by reacting 1.1 moles of cyclohexanone with 1 mole of TMD in the presence of hydrogen and 1.5 wt % (dry basis) Pd/C (Aldrich, Degussa Type E101 N/OW). A 1-liter Parr pressure reactor was charged with 355.4 g of TMD, 5.35 g of Pd/C (dry weight), and 243.9 g of reagent grade cyclohexanone. The reactor was sealed and pressure cycled 3 times each with nitrogen to remove the air, and then with hydrogen to remove the nitrogen. The reactor was then heated to 80° C. and pressurized to 120 psig with hydrogen, while stirring at 750-1000 rpm. The temperature was held at 80° C. for approximately 50 min, then the temperature was increased to 120° C. and the hydrogen pressure was increased to 800 psig. These conditions were maintained for 180 min. Then, the reaction temperature was increased to 130° C. for approximately 1 hour to complete the reaction. Reactor contents were cooled to 40° C. and then removed. After rotary evaporation, the resulting TMD-1 composition was 74% N-cyclohexyl-TMD, 22% N,N'-dicyclohexyl-TMD, and 4% TMD, by weight.

Examples 19-20 utilized compositions containing DM-MXDA and a plasticizer or solvent, namely benzyl alcohol. The amine-epoxy compositions of Examples 19 and 20 had a calculated stoichiometric ratio of epoxy equivalents of the epoxy resin to amine equivalents of Example 9 of about 1:1 and about 4:1, respectively. Example 19 produced coatings with excellent gloss and good early hardness development at ambient conditions and at 5° C. Further, the coating of Example 19 dried relatively quickly, as can be seen by comparing the thin film set time of Example 19 to that of Examples 10, 12, and 13 at ambient temperature and at 5° C. The coating of Example 20 demonstrated that DM-MXDA is an effective curing agent for curing epoxy resin, even at very low amounts of active hydrogen. That is, Example 20 used only 23 amine hydrogen equivalents per 100 equivalents of epoxy, yet still produced coatings with high gloss and good initial hardness at an ambient temperature cure. At 5° C., cure speed was reduced, but hard coatings were obtained over time.

Examples 21-22 and 24-25 utilized compositions containing Example 9 (approximately 88% DM-MXDA), at least one multifunctional amine, and a plasticizer or solvent. Examples 21-22 used MPCA as at least one multifunctional amine, Example 24 used MXDA, and Example 25 used IPDA. Example 26 employed DM-MXDA and at least one multifunctional amine, CX-105, but did not contain a plasticizer or solvent.

The coating compositions of Examples 21-22 had a low mix viscosity, thus enabling the use of high solids, as compared to, for instance, Examples 10-12 and 14. In comparison to Examples 10-13, the coatings of Examples 21-22 gave improved cure speed and hardness at both ambient temperature and at 5° C., and superior flexibility as indicated in the Mandrel Bend test, Schedule B. Examples 21-22 provided a combination of low mix viscosity, fast dry speed, high early hardness and excellent impact resistance, particularly following schedule B, that can be found in Examples 14-18, but not in Examples 10-13.

When compared to Examples 21-22, Examples 24-25 demonstrated similar mix viscosities. The coating of Example 24 provided moderate gloss and flexibility, but was subject to carbamation. It appears that the carbamation may be related to the use of MXDA as the multifunctional amine, as illustrated by Example 23.

Surprisingly, the coatings of Examples 22 and 26 demonstrated high pore resistance and low water uptake which was comparable to that of Examples 10-13. As such, the coatings of Examples 22 and 26 demonstrated high barrier properties, which is an important feature in metal protection applications, such as the coating of metal substrates. The barrier properties (pore resistance, water uptake) of the coatings of Examples 22 and 26, which contain DM-MXDA, were significantly better than the barrier properties of Examples 14-18.

The coatings of Examples 27-28 also demonstrated high pore resistance and low water uptake, and exhibited similar properties to those of Examples 21-22 at 25° C., with exception of a reduced gloss (matte) appearance. Examples 29-30 employed TMD-1 and exhibited both slow drying speed and slow hardness development at 25° C., as compared to, for instance, Examples 21-22. Similarly, at 5° C., Examples 29-30 had long cure times and, due to the tackiness of the respective coatings, Persoz Hardness could not be measured.

TABLE 6

Examples 19-30 cured at 25° C. or following cure schedules A-B.

| | Example 19 | | Example 20 | | Example 21 | | Example 22 | |
|---|---|---|---|---|---|---|---|---|
| Hardener Composition (Parts by Weight) | EX-9<br>BA | 100<br>36 | EX-9<br>BA | 100<br>110 | EX-9<br>MPCA<br>BA | 75<br>25<br>43 | EX-9<br>MPCA<br>BA | 65<br>35<br>43 |
| Use Level (PHR) with DGEBA | 58 | | 21 | | 56 | | 53 | |
| Mix Viscosity (mPa · s) | — | | — | | 900 | | 1,170 | |
| Coating Solids (weight %) | 90 | | 91 | | 89 | | 90 | |
| Thin Film Set Time (h) Phase 2/Phase 3 | 2.4/3.4 | | — | | 3.0/4.0 | | 3.2/4.3 | |
| Coating Appearance Specular Gloss 20°/60° Visual | 105/104<br>high gloss | | 105/103<br>high gloss | | 102/100<br>high gloss | | 106/103<br>high gloss | |
| Persoz Hardness (s) Day 1/Day 7 | 206/— | | 115/— | | 300/340 | | 290/330 | |
| Impact Resistance (kg · cm) Direct/Reverse Schedule A | — | | — | | 45/— | | 45/— | |
| Schedule B | — | | — | | 190/105 | | 200/85 | |
| Mandrel Bend (% elongat.) Schedule B | — | | — | | 29 | | 29 | |
| EIS Resistance Data Pore Resistance, 24 h (Ω) | — | | — | | — | | 2 × 10$^8$ | |
| Water Uptake, 24 h (wt %) | — | | — | | — | | 3 | |

| | Example 23 | | Example 24 | | Example 25 | | Example 26 | |
|---|---|---|---|---|---|---|---|---|
| Hardener Composition (Parts by Weight) | MXDA<br>BA | 100<br>43 | EX-9<br>MXDA<br>BA | 70<br>30<br>43 | EX-9<br>IPDA<br>BA | 75<br>25<br>60 | EX-9<br>CX105 | 75<br>25 |
| Use Level (PHR) with DGEBA | 26 | | 42 | | 56 | | 45 | |
| Mix Viscosity (mPa · s) | — | | 640 | | — | | — | |
| Coating Solids (weight %) | 94 | | 91 | | 87 | | 100 | |
| Thin Film Set Time (h) Phase 2/Phase 3 | —/— | | 4.2/5.0 | | 3.9/5.5 | | —/— | |
| Coating Appearance Specular Gloss 20°/60° Visual | 40/68<br>mild carbamate | | 59/89<br>glossy | | 103/103<br>high gloss | | —/— | |
| Persoz Hardness (s) Day 1/Day 7 | —/— | | 305/340 | | 270/335 | | —/— | |
| Impact Resistance (kg · cm) Direct/Reverse Schedule A | 45/— | | 60/— | | —/— | | —/— | |
| Schedule B | 80/30 | | 85/40 | | —/— | | —/— | |
| Mandrel Bend (% elongat.) Schedule B | — | | — | | — | | — | |
| EIS Resistance Data Pore Resistance, 24 h (Ω) | — | | — | | — | | 2 × 10$^{10}$ | |
| Water Uptake, 24 h (wt %) | — | | — | | — | | <1 | |

| | Example 27 | | Example 28 | | Example 29 | | Example 30 | |
|---|---|---|---|---|---|---|---|---|
| Hardener Composition (Parts by Weight) | EX-9<br>1,3-BAC<br>BA | 75<br>25<br>43 | EX-9<br>1,3-BAC<br>BA | 60<br>40<br>43 | TMD-1<br>MPCA<br>BA | 75<br>25<br>60 | TMD-1<br>MPCA<br>BA | 63<br>37<br>43 |
| Use Level (PHR) with DGEBA | 46 | | 40 | | 58 | | 52 | |

TABLE 6-continued

Examples 19-30 cured at 25° C. or following cure schedules A-B.

| | | | | |
|---|---|---|---|---|
| Mix Viscosity (mPa · s) | 450 | 500 | 920 | 1270 |
| Coating Solids (weight %) | 91 | 91 | 89 | 90 |
| Thin Film Set Time (h) | | | | |
| Phase 2/Phase 3 | 2.8/3.2 | 2.8/3.2 | 8.3/10.2 | 7.8/9.9 |
| Coating Appearance | | | | |
| Specular Gloss 20°/60° | 70/81[a] | 45/55[a] | 170/142[a] | 170/143[a] |
| Visual | matte | matte | high gloss | high gloss |
| Persoz Hardness (s) | | | | |
| Day 1/Day 7 | 301/325 | 301/322 | 177/331 | 180/327 |
| Impact Resistance (kg · cm) Direct/Reverse | | | | |
| Schedule A | 40/<5 | 40/<5 | 40/<5 | 40/<5 |
| Schedule B | —/— | —/— | —/— | —/— |
| Mandrel Bend (% elongat.) | | | | |
| Schedule B | — | — | — | — |
| EIS Resistance Data | | | | |
| Pore Resistance, 24 h (Ω) | $2.4 \times 10^9$ | $1.1 \times 10^9$ | $9.8 \times 10^8$ | $2.1 \times 10^9$ |
| Water Uptake, 24 h (wt %) | 5 | 6 | 8 | 7 |

[a]Gloss measurements for Examples 27-30 were conducted using a glass panel background instead of a matte paper background. Generally, a gloss reading of about 140-170 using a glass background correlates to a gloss reading of at least 95 using the matte paper background employed in Examples 19-26.

TABLE 7

Examples 19-30 cured at 5° C.

| | Example | | | |
|---|---|---|---|---|
| | 19 | 20 | 21 | 22 |
| Thin Film Set Time (h) | | | | |
| Phase 2/Phase 3 | 9.2/9.8 | 18.1/21.4 | 6.5/8.1 | 7.0/9.4 |
| Coating Appearance | | | | |
| Specular Gloss 20°/60° | 11/40 | 98/100 | 84/95 | 89/98 |
| Visual | carbamated | high gloss | high gloss | high gloss |
| Persoz Hardness (s) | | | | |
| Day 2/Day 7 | 190/275 | 11/140 | 110/— | 110/235 |

| | Example | | | |
|---|---|---|---|---|
| | 23 | 24 | 25 | 26 |
| Thin Film Set Time (h) | | | | |
| Phase 2/Phase 3 | —/— | 10.6/12.8 | 8.0/12.4 | 4.8/5.6 |
| Coating Appearance | | | | |
| Specular Gloss 20°/60° | 11/40 | 17/46 | 20/43 | —/— |
| Visual | strong carbamation | mild carbamate | mild carbamate | |
| Persoz Hardness (s) | | | | |
| Day 2/Day 7 | —/— | 55/280 | 46/300 | —/— |

| | Example | | | |
|---|---|---|---|---|
| | 27 | 28 | 29 | 30 |
| Thin Film Set Time (h) | | | | |
| Phase 2/Phase 3 | 6.7/9.0 | 9.6/>24 | 25.5/31.5 | 23/27.5 |
| Coating Appearance | | | | |
| Specular Gloss 20°/60° | 9/31[a] | 2/14[a] | 68/84[a] | 93/105[a] |
| Visual | matte greasy | matte greasy | glossy | glossy |
| Persoz Hardness (s) | | | | |
| Day 2/Day 7 | 27/— | 27/— | tacky | tacky |

[a]Gloss measurements for Examples 27-30 were conducted using a glass panel background instead of a matte paper background. Generally, a gloss reading of about 140-170 using a glass background correlates to a gloss reading of at least 95 using the matte paper background employed in Examples 19-26.

Example 31

Preparation of an Epoxy Floor Composition

A flooring composition containing epoxy resin, pigment, filler, and other additives was prepared in a 1-liter container using a laboratory dissolver (Dispermat® CV, VMA-Getzmann GmbH) equipped with a 6-cm diameter dissolver blade (VMA-Getzmann GmbH). The following materials were placed in the 1-liter container and mixed at approximately 1500 rpm until the mixture was homogeneous: 336 g of bisphenol-A/F epoxy resin (D.E.R. 352, EEW 172-181, Dow Chemical Company); 69 g of glycidyl ether of $C_{12}$-$C_{14}$ alcohol (Epodil® 748, EEW 275-300, Air Products and Chemicals, Inc.); 15 g of Byk® 057 (Byk Chemie, defoaming aid); and 10 g Dynol™ 604 (Air Products and Chemicals, Inc., leveling aid). Next, 100 g of titanium dioxide (Kronos® 2160, Kronos) and 470 g of barium sulfate (Barytmehl F, Sachtleben Chemie GmbH) were added and mixed at a low speed until the mixture was homogeneous. The speed was then increased to 4000 rpm for 15 minutes to homogenize the coarse pigment and filler particles, at which point the temperature increased to 50° C. The maximum particle size of the mixture was determined to be less than 20 μm, using a fineness of grind gage (Precision Gage Tool Co., model 5250).

Subsequently, the mixture was cooled to ambient temperature. Formulations like Example 31, when mixed with an amine curing agent, and optionally sand, are well-known to those skilled in the art and are often referred to as self-levelers, self-leveling floor systems, or other similar terminology.

Examples 32-36

Amine-Epoxy Floor Compositions

Examples 32-35 illustrate the properties obtained from mixing the exemplary floor formulation of Example 31, sand (particle size of 0.2-0.4 mm), and an amine composition containing DM-MXDA, at least one multifunctional amine, and a plasticizer or solvent. Example 36 employed an amine composition which contained A1618, a cycloaliphatic amine adduct, but did not contain DM-MXDA.

Approximately 100 parts of sand, 100 parts of the formulation of Example 31, and 18-24 parts of the respective amine hardener composition were mixed. Table 8 summarizes the components used and the properties of the amine-epoxy floor formulations. As shown in Table 8, each of Examples 32-35 had comparable flow and Shore A and D hardness development (at a coating thickness of 2 mm) to that of Example 36. Of Examples 32-35, Example 33 had the longest gel time, indicating a longer working time before cure.

TABLE 8

Compositions and Properties of Examples 32-36 cured at 23° C.

| | Example | | | | |
|---|---|---|---|---|---|
| | 32 | 33 | 34 | 35 | 36 |
| Hardener Composition (Parts by weight) | EX-9 75<br>IPDA 25<br>BA 60 | EX-9 68<br>IPDA 32<br>BA 60 | EX-9 75<br>1,3-BAC 25<br>BA 60 | EX-9 60<br>1,3-BAC 40<br>BA 60 | A1618 |
| Parts of hardener composition | 21.6 | 22.2 | 21.5 | 18.9 | 23.4 |
| Parts of Example 31 | 100 | 100 | 100 | 100 | 100 |
| Parts of sand | 100 | 100 | 100 | 100 | 100 |
| Gel time (min) | 89 | 140 | 95 | 75 | 477 |
| Flow (mm) | 108 | 103 | 106 | 100 | 107 |
| Appearance | | | | | |
| Specular Gloss 20°/60° | 73/99 | 92/101 | 74/100 | 56/92 | 90/99 |
| Visual | glossy | glossy | matte | matte | glossy |
| Shore A/D Hardness | | | | | |
| 16 hours | 85A | 35D | 40D | 40D | 86A |
| 24 hours | 55D | 50D | 58D | 60D | 50D |
| 7 days | 76D | 74D | 75D | 75D | 74D |

We claim:

1. An amine curing agent composition for epoxy containing compositions comprising:
   (i) N,N'-dimethyl-meta-xylylenediamine (DM-MXDA);
   (ii) at least one multifunctional amine comprising at least one member selected from the group consisting of N-monomethyl-meta-xylylenediamine (MM-MXDA), phenalkamine; 1,3-bis(aminomethyl)cyclohexane; a mixture of methylene bridged poly(cyclohexyl-aromatic)amines (MPCA); and any combination thereof; wherein the ratio of DM-MXDA to the at least one multifunctional amine ranges from about 95:5 to about 5:95; and
   (iii) at least one plasticizer or solvent.

2. The amine curing agent composition of claim 1, wherein the at least one plasticizer or solvent comprises benzyl alcohol, n-butanol, xylene, methyl ethyl ketone, nonyl phenol, dodecyl phenol, cardanol, an ester of phthalic acid, or any combination thereof.

3. The amine curing agent composition of claim 1, wherein the weight ratio of DM-MXDA to the at least one multifunctional amine is in a range from about 55:45 to about 90:10.

4. The amine curing agent composition of claim 1, wherein the at least one multifunctional amine comprises N-monomethyl-meta-xylylenediamine (MM-MXDA).

5. An amine-epoxy composition comprising:
   (a) the amine curing agent composition of claim 1; and
   (b) an epoxy component comprising at least one multifunctional epoxy resin.

6. The amine-epoxy composition of claim 5, wherein a stoichiometric ratio of epoxy groups in the epoxy component to amine hydrogens in the amine composition ranges from about 2:1 to about 1:1.2.

7. A process comprising curing the amine-epoxy composition of claim 5.

8. An article of manufacture obtained by the process of claim 7.

9. The article of manufacture of claim 8 which is a coating, construction product, flooring product or a composite product.

10. The curing agent composition of claim 5 wherein the composition cures the epoxy containing compositions at a temperature of less than about 25C.

11. The composition of claim 5 wherein the at least one multifunctional epoxy resin comprises DGEBA.

12. The composition of claim 1 wherein the DM-MXDA comprises a mixture of amines and the mixture of amines is produced by a process comprising:
   (a) contacting 1,3-dicyanobenzene with mono-methylamine in the presence of hydrogen and a catalyst at a hydrogen pressure of about 100 to about 500 psi to form at least one intermediate product; and,
   (b) contacting the at least one intermediate product with hydrogen in the presence of a hydrogenation catalyst at a hydrogen pressure of about 400 to about 1500 psi to form the mixture of amines comprising DM-MXDA.

13. The composition of claim 1 wherein the composition comprises DM-MXDA, MM-MXDA and at least one other multifunctional amine.

14. The composition of claim 13 wherein the at least one other multifunctional amine comprises MPCA.

15. The composition of claim 1 wherein the composition comprises DM-MXDA, MM-MXDA and at least one phenalkamine.

16. The composition of claim 1 wherein the composition comprises DM-MXDA, MM-MXDA and meta-xylylene diamine (MXDA).

17. The composition of claim 1 wherein composition comprises DM-MXDA, MM-MXDA and 1,3-bis(aminomethyl)cyclohexane.

18. The composition of claim 1 wherein the composition comprises DM-MXDA, MM-MXDA and a mixture of methylene bridged poly(cyclohexyl-aromatic) amines(MPCA).

* * * * *